(12) United States Patent
Levinson

(10) Patent No.: US 6,398,796 B2
(45) Date of Patent: Jun. 4, 2002

(54) SUTURE WITH TOGGLE AND DELIVERY SYSTEM

(75) Inventor: Melvin E. Levinson, Miami, FL (US)

(73) Assignee: Scion Cardio-Vascular, Inc., Miami, FL (US)

( * ) Notice: Subject to any disclaimer, the term of this patent is extended or adjusted under 35 U.S.C. 154(b) by 0 days.

(21) Appl. No.: 09/757,748

(22) Filed: Jan. 10, 2001

Related U.S. Application Data

(63) Continuation-in-part of application No. 09/668,327, filed on Sep. 22, 2000, now Pat. No. 6,245,080, which is a continuation of application No. 09/661,024, filed on Sep. 13, 2000, now Pat. No. 6,319,263, which is a continuation of application No. 09/413,145, filed on Oct. 6, 1999, now Pat. No. 6,206,895.
(60) Provisional application No. 60/143,555, filed on Jul. 13, 1999.

(51) Int. Cl.[7] ................................ A61B 17/04
(52) U.S. Cl. ............. 606/144; 606/145; 606/220; 606/221
(58) Field of Search ................. 606/139, 144, 606/145, 213, 215

(56) References Cited

U.S. PATENT DOCUMENTS

| 3,675,639 A | * | 7/1972 | Cimber ........................... 128/1 |
| 4,006,747 A | | 2/1977 | Kronenthal et al. ........ 128/335 |
| 4,669,473 A | | 6/1987 | Richards et al. ............ 128/334 |
| 4,705,040 A | | 11/1987 | Mueller et al. ......... 128/334 R |
| 4,741,330 A | | 5/1988 | Hayhurst ................ 128/92 YF |
| 4,744,364 A | | 5/1988 | Kensey ................... 128/334 R |
| 5,041,129 A | * | 8/1991 | Hayhurst et al. ............ 606/232 |
| 5,053,046 A | | 10/1991 | Janese ........................ 606/215 |
| 5,474,573 A | * | 12/1995 | Hatcher ....................... 606/232 |
| 5,860,990 A | | 1/1999 | Nobles et al. ............... 606/144 |
| 5,868,792 A | * | 2/1999 | Cragg et al. ................ 606/144 |

* cited by examiner

Primary Examiner—Gary Jackson
(74) Attorney, Agent, or Firm—Robert C. Kain, Jr.; Fleit, Kain

(57) ABSTRACT

The suture delivery system utilizes two sutures. Each suture has a filament body and a toggle bar. The delivery system includes an elongated central tube with two needle retainer guides and a cam distally disposed on the central tube. The needles have piercing needle ends and each needle end carries a respective toggle bar for a suture disposed thereon. A longitudinally movable member is coupled to the needles. The needles are movably disposed in respective needle retainer guides. An actuator is coupled to the movable member such that when the actuator moves, the needles extend outward such that the needle ends move over the cam. In a further embodiment, the actuator includes a first user actuation surface coupled to the movable member and the central tube includes a second user actuation surface which is generally static. In a further embodiment, a locking member is disposed on the second user actuation surface. The cam may take one of a variety of shapes. Essentially, the needle ends splay outward and forward, distally over the cam. In a preferred embodiment, the movable member is biased with respect to the central tube such that the delivery system is biased to place the needles in the proximal position and the needle ends are substantially captured in the guides. A method for embedding sutures in a vascular wall or other biological substructure is also included.

69 Claims, 24 Drawing Sheets

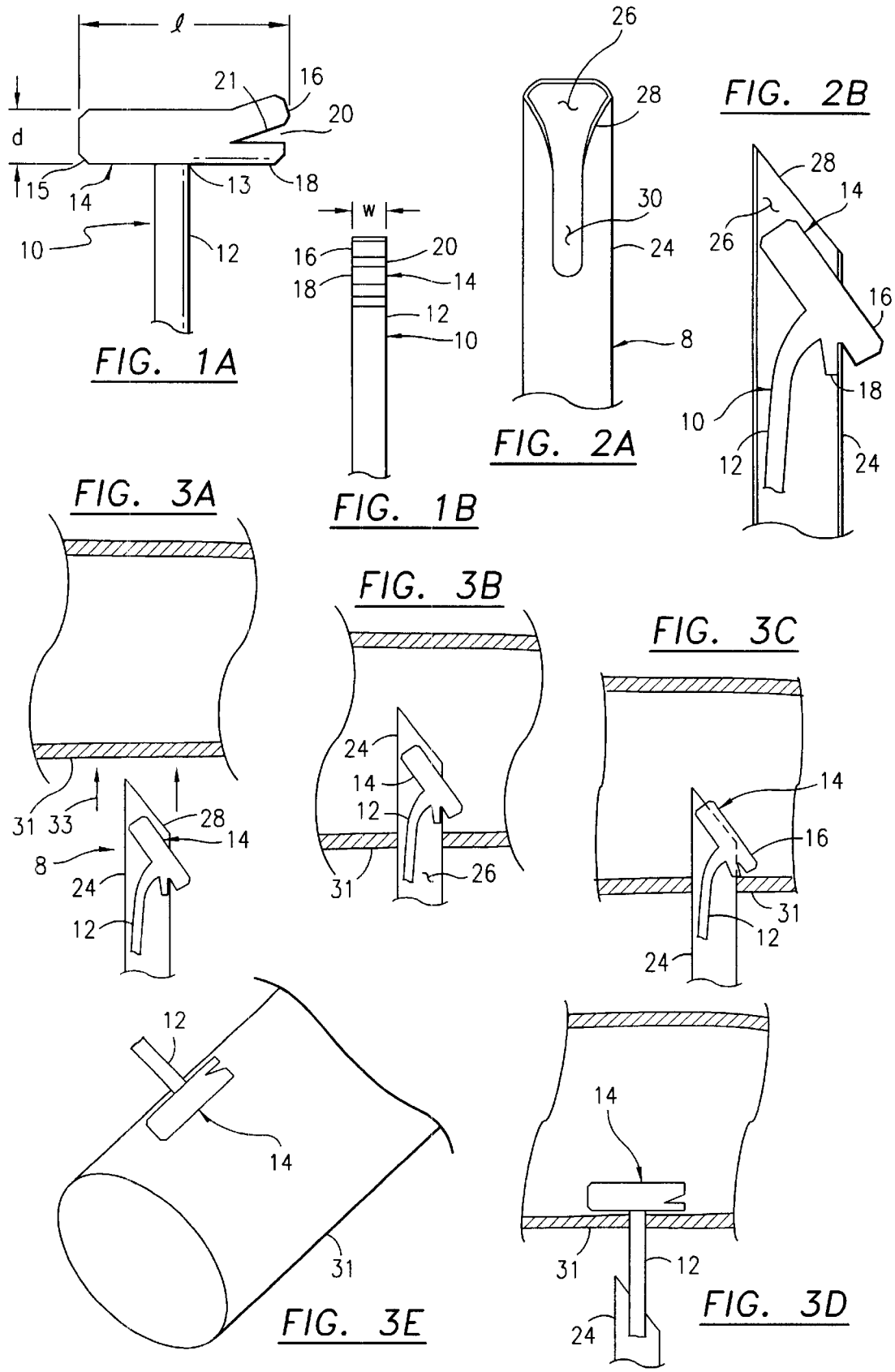

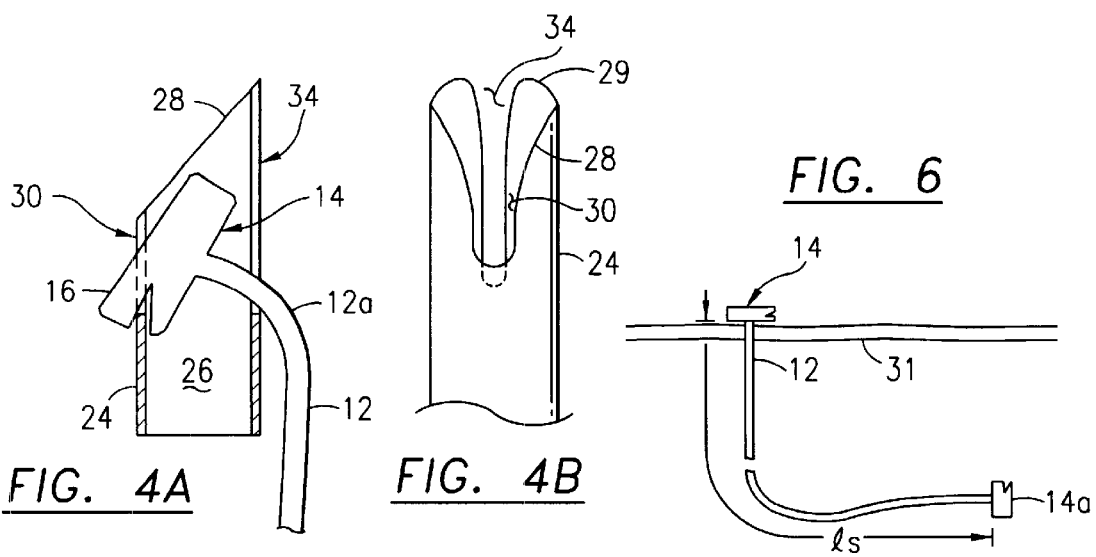
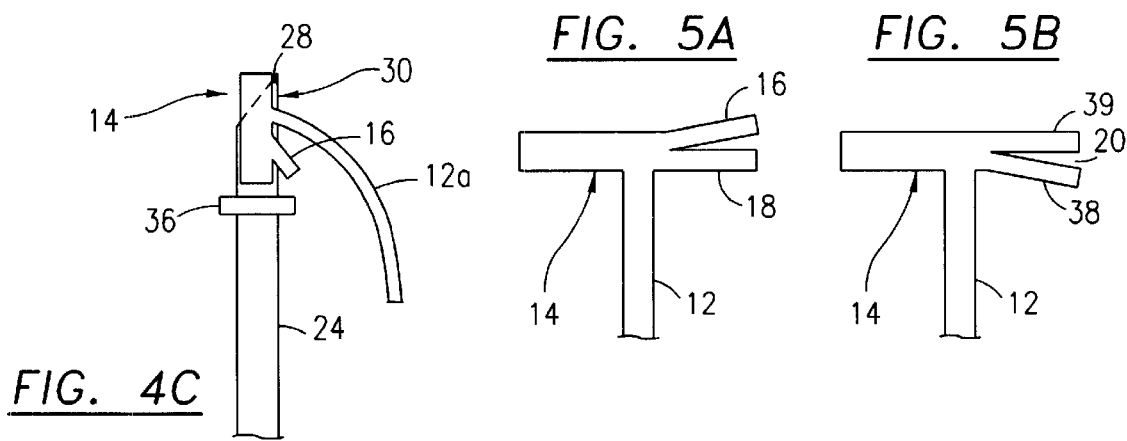
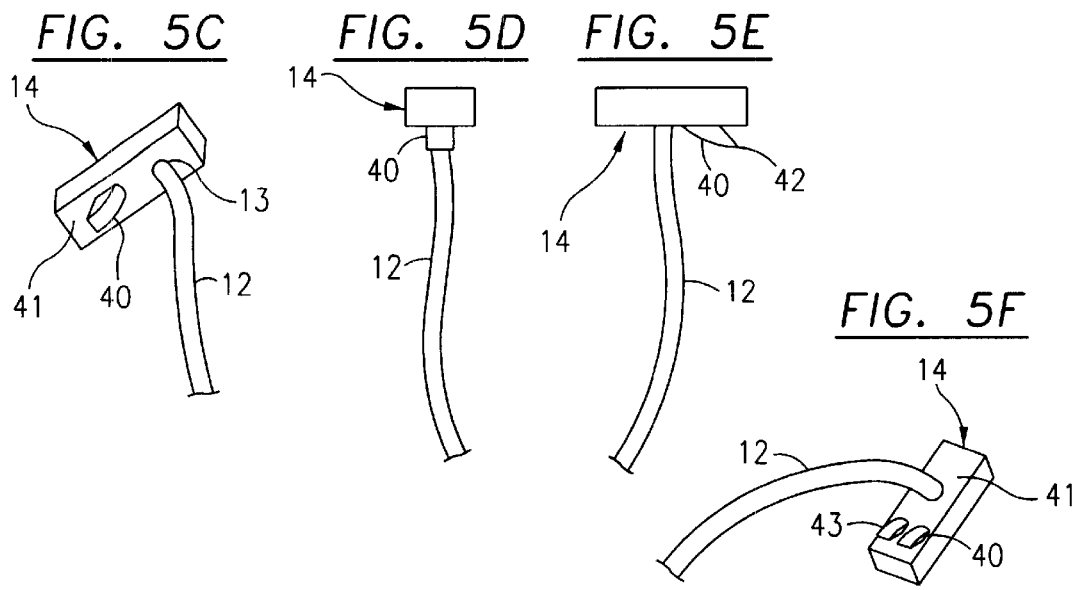

FIG. 8A
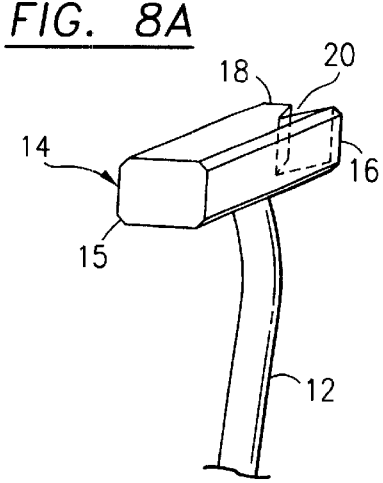
FIG. 8B
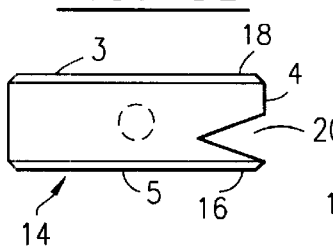
FIG. 8C
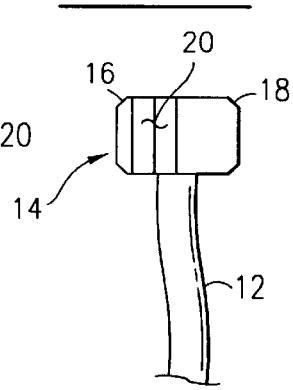
FIG. 9A
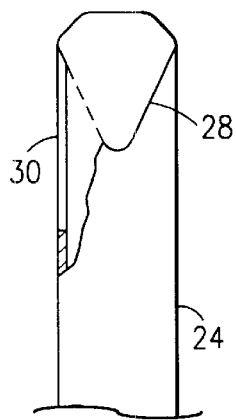
FIG. 9B
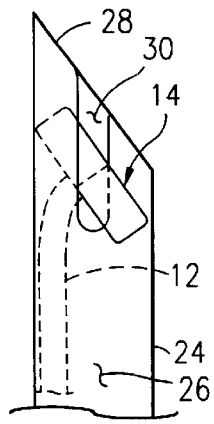
FIG. 9C
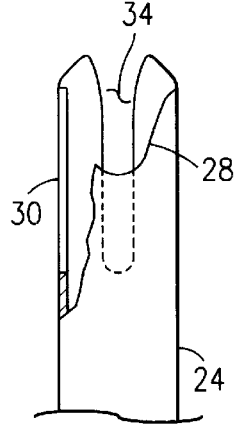
FIG. 9D
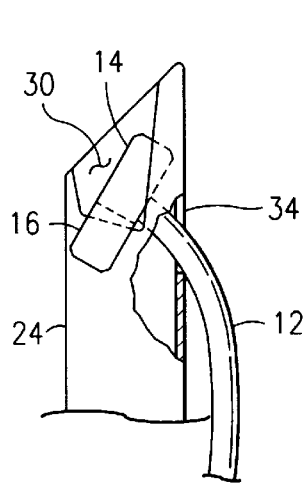
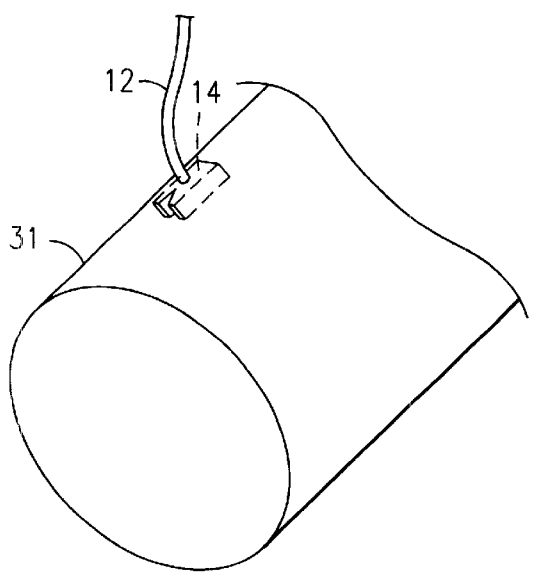
FIG. 10A
FIG. 10B
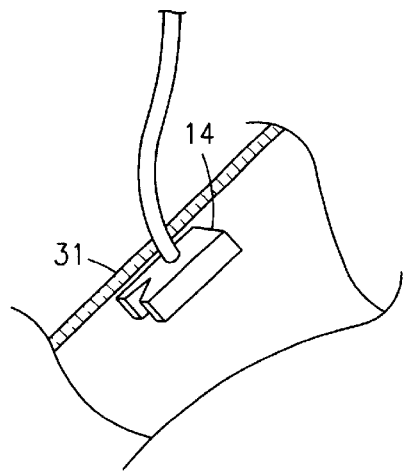

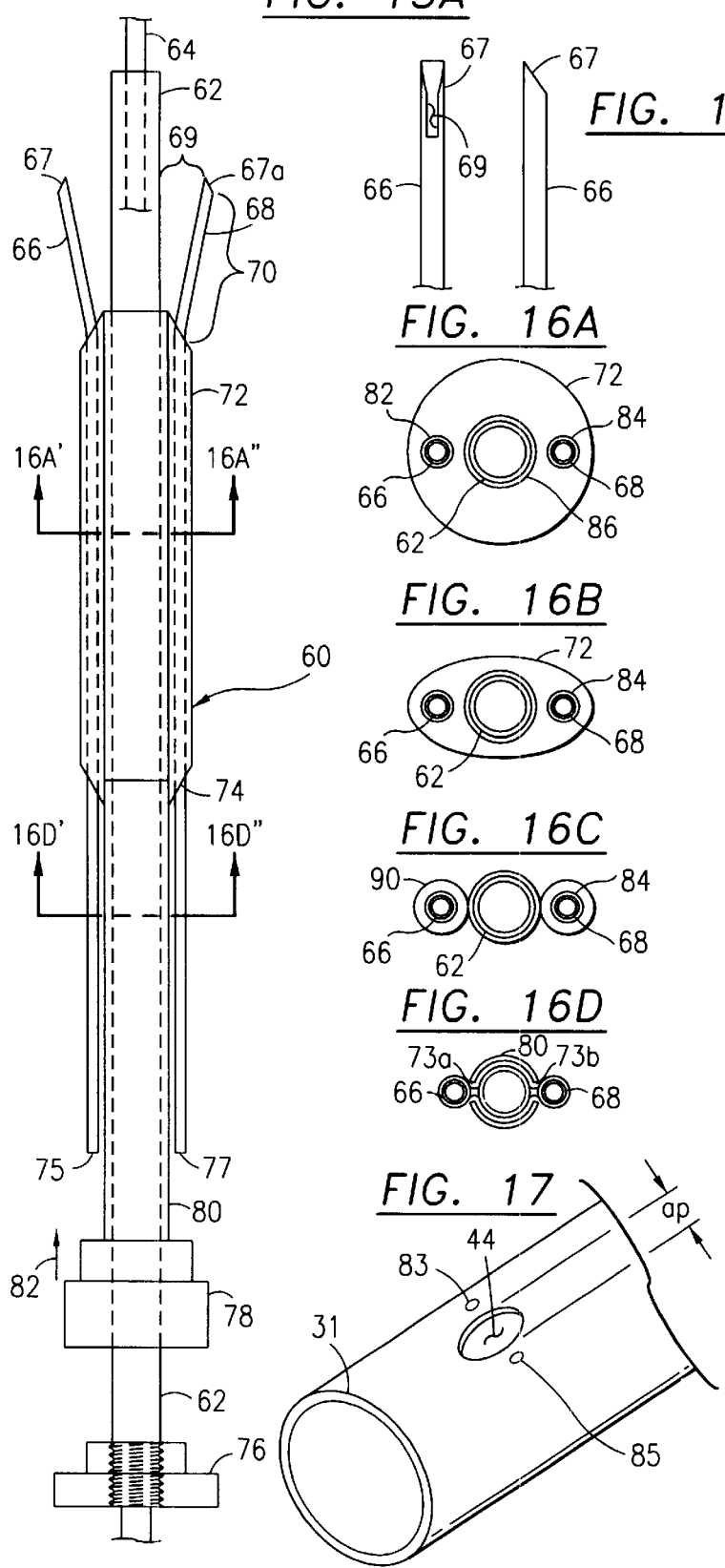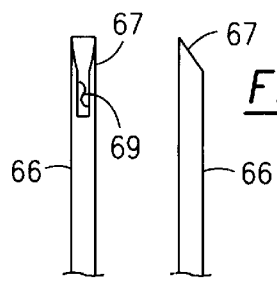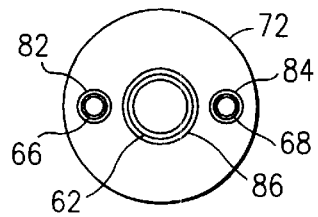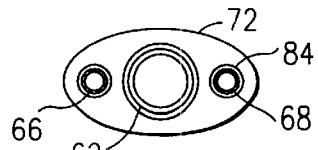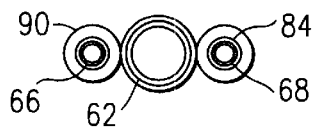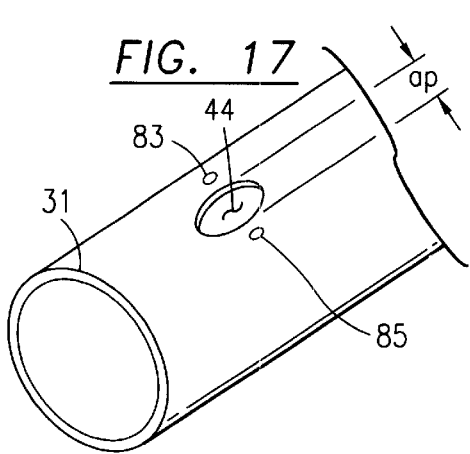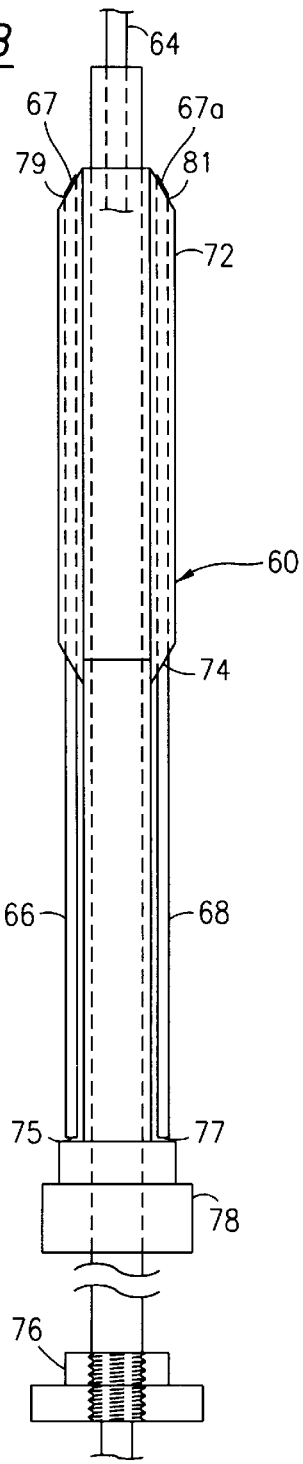

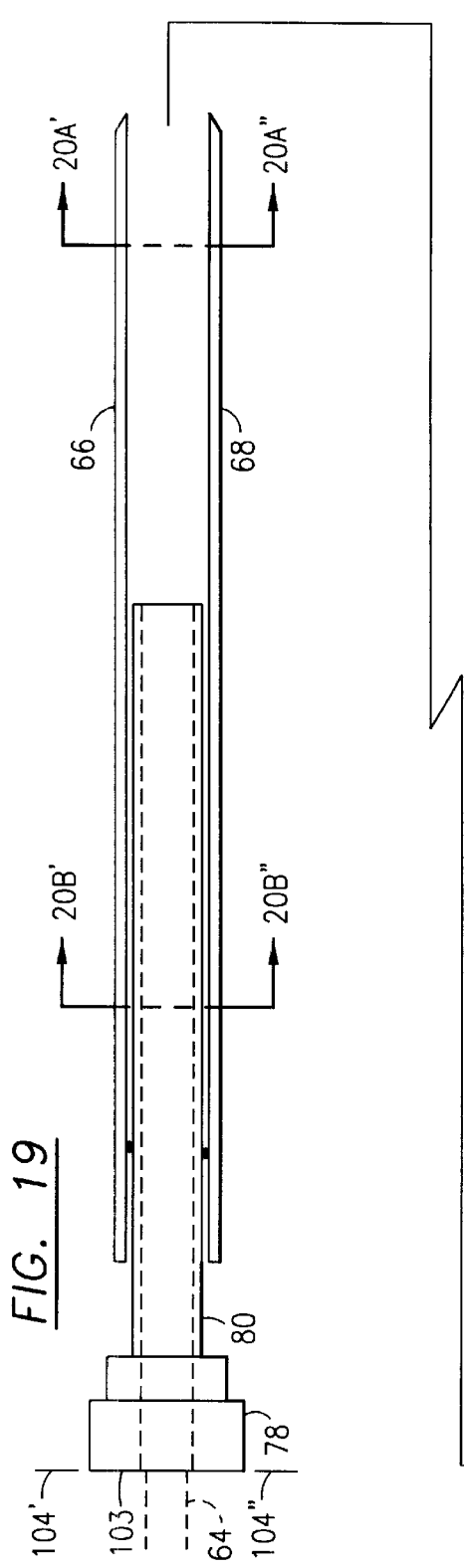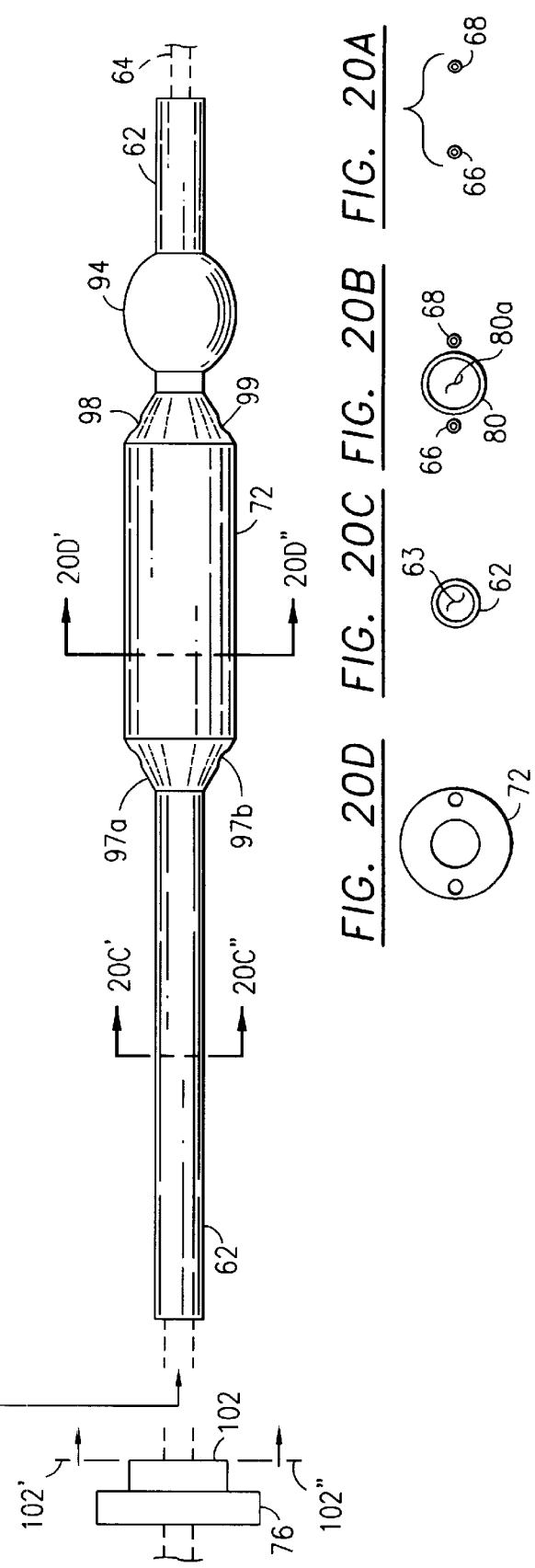

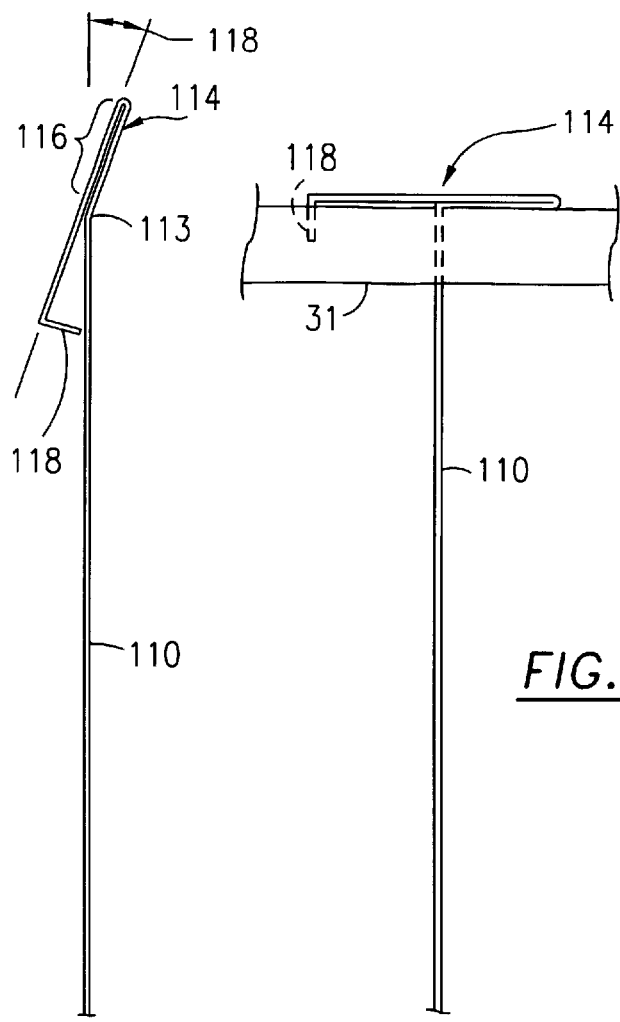
FIG. 21A
FIG. 21B
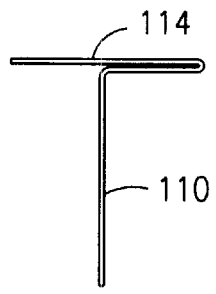
FIG. 21C
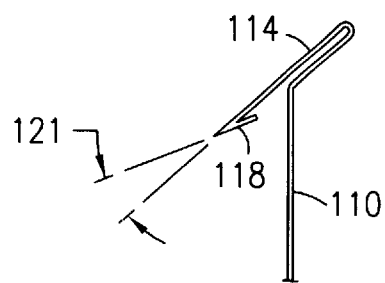
FIG. 21D

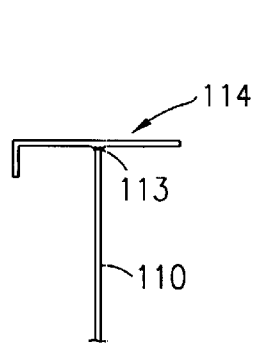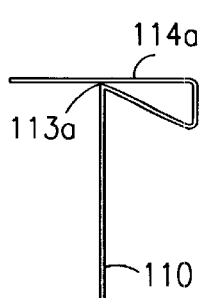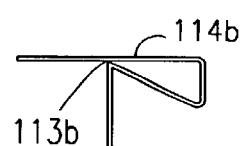
FIG. 21E
FIG. 21F
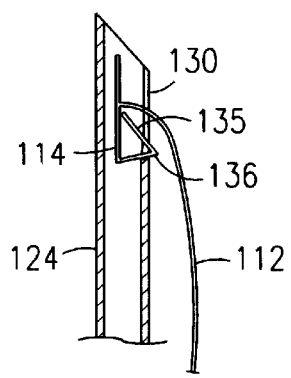
FIG. 22A
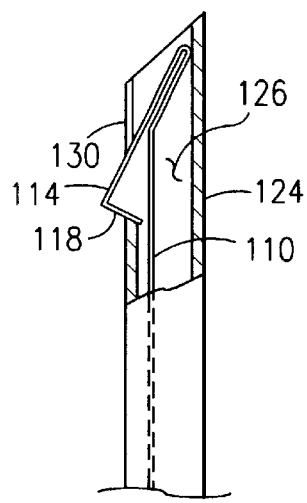
FIG. 22B
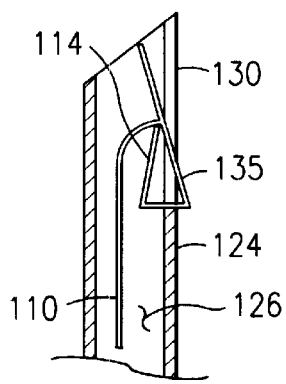
FIG. 22C
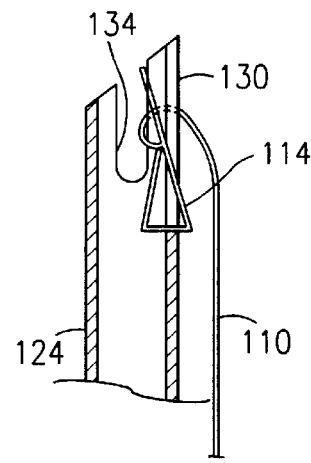
FIG. 22D

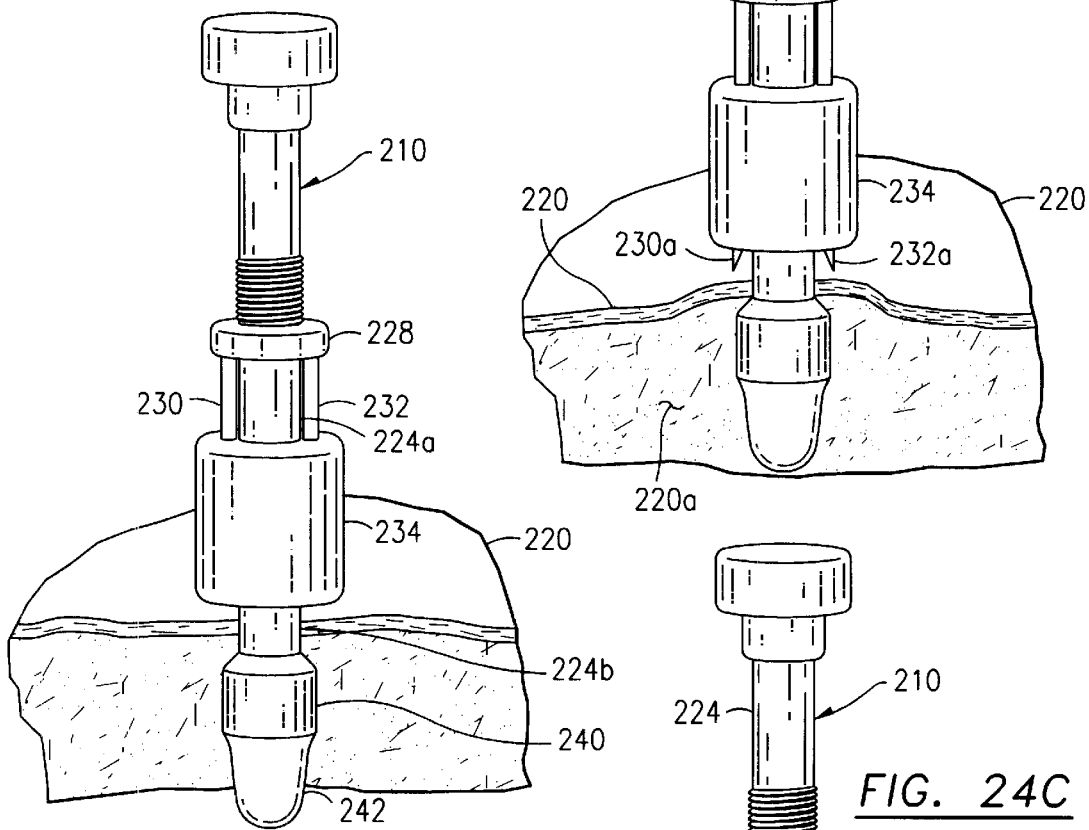

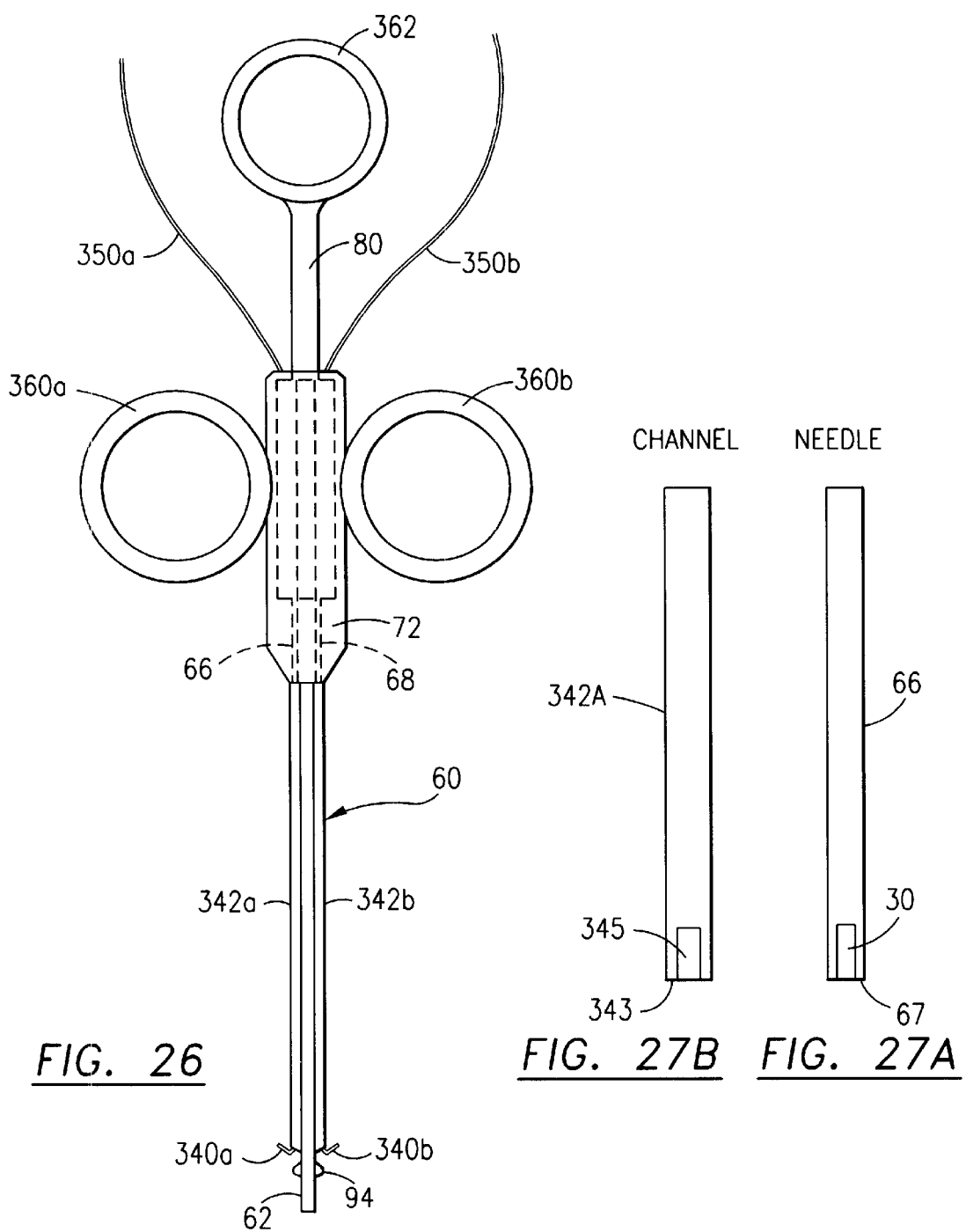

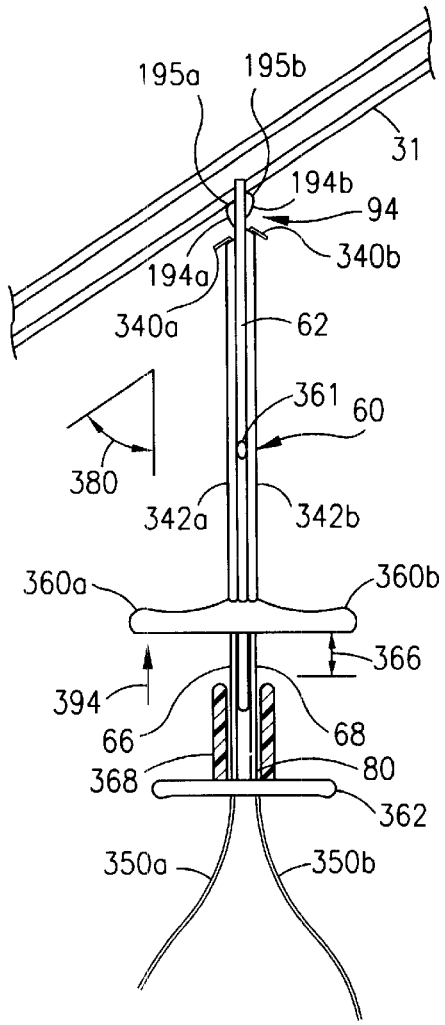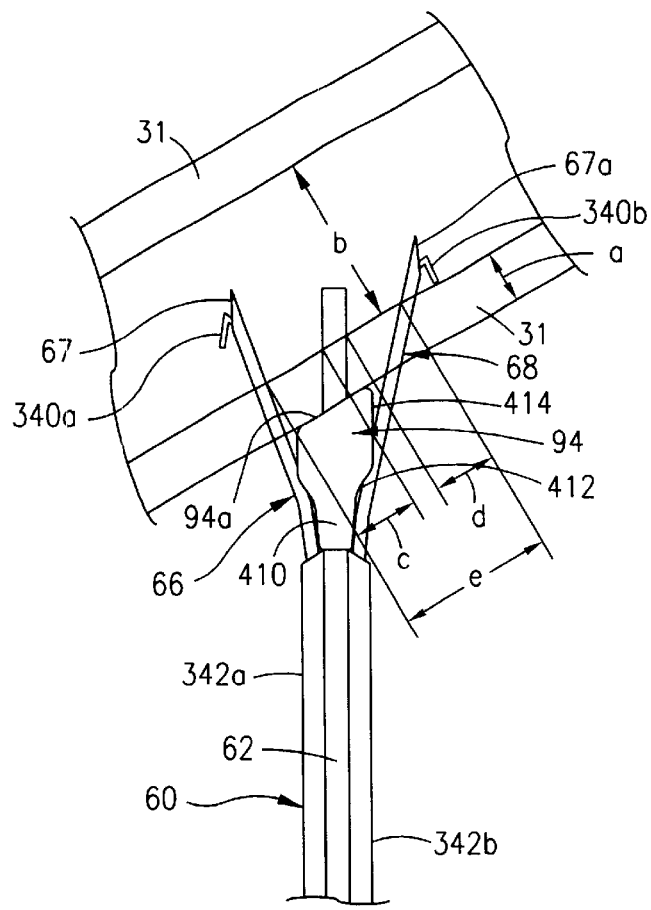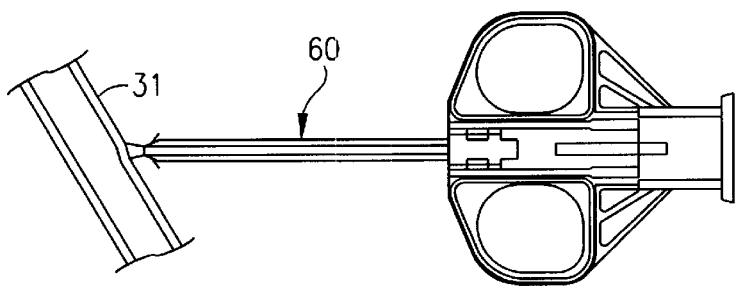
FIG. 28B
FIG. 28C
FIG. 28A

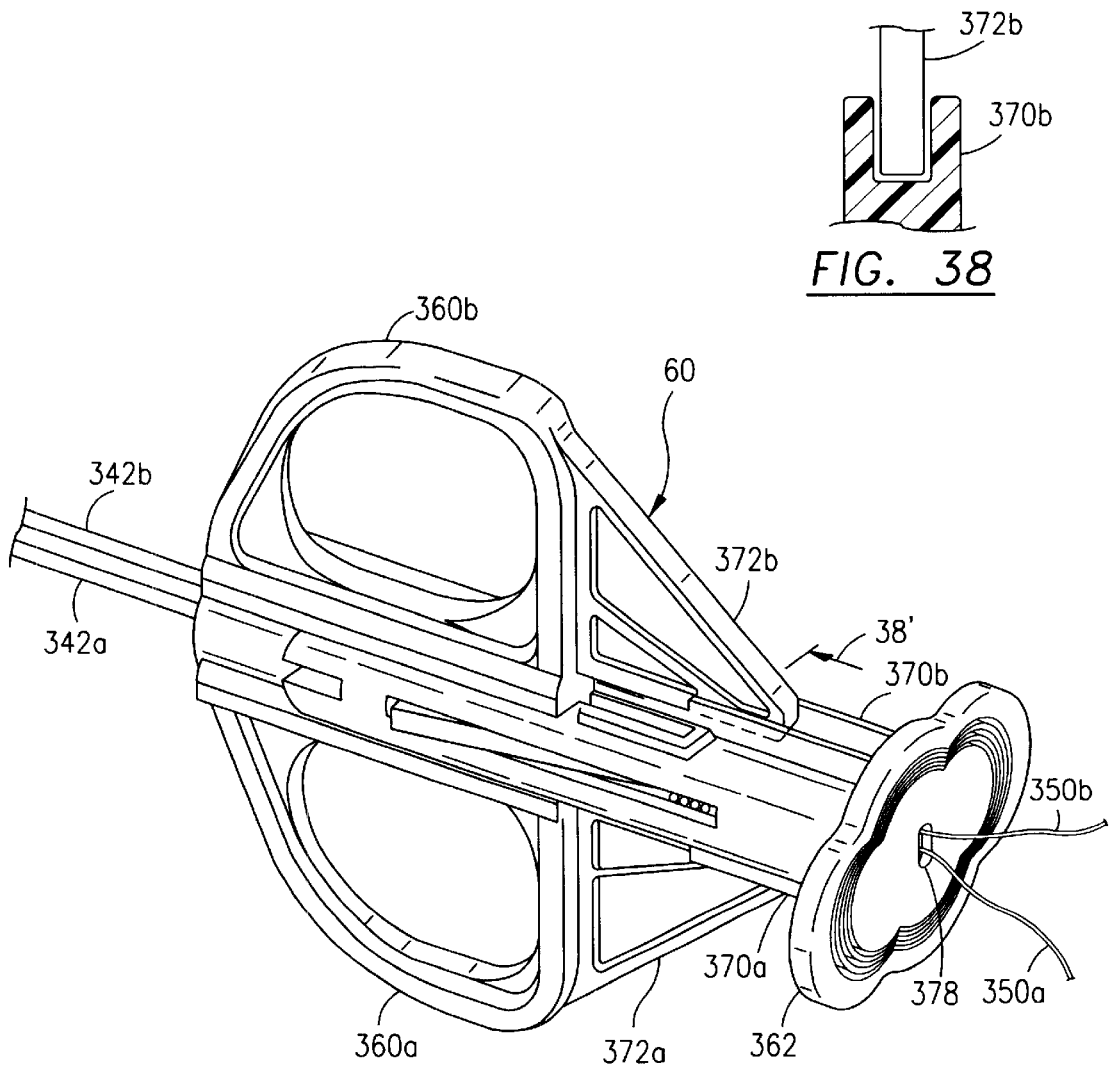

SUTURE WITH TOGGLE AND DELIVERY SYSTEM

This is a continuation-in-part of patent application Ser. No. 09/668,327 filed on Sep. 22, 2000, now U.S. Pat. No. 6,245,080, which is a continuation of patent application Ser. No. 09/661,024 filed on Sep. 13,2000, now U.S. Pat. No. 6,319,263 which is a continuation of patent application Ser. No. 09/413,145 filed on Oct. 6, 19991, now U.S. Pat. No. 6,206,895 which is a regular patent application based upon provisional patent application Ser. No. 60/143,555 filed on Jul. 13, 1999.

BACKGROUND OF THE INVENTION

In order to pass a suture through a tubular organ or other structure in a body (a human body or an animal), it is necessary to traverse the bodily structure, tissue or organ completely and encircle the area where the physician or medical technician wishes to place the suture. This traverse and encircle method works well in situations where easy access is available to the structure, tissue or organ and the item to be sutured is easily viewed by the physician. In limited access situations (for example, in laposcopic surgery, cardiac surgery and vascular surgery), the traverse and encirclement by sutures is often times difficult, dangerous and at other times impossible.

As a further example, an attempt to suture a blood vessel through a small puncture wound is almost impossible. The direct suture of the arterial puncture is not possible.

The increasing utilization of minimally invasive surgical techniques has created a need for improved methods, suture systems and suture placement devices under adverse conditions of limited access and limited visibility of the suture site.

U.S. Pat. No. 5,053,046 to Janese discloses a dural sealing needle. The dural sealing needle includes a gelatin sealing compound that swells and sits between an impact cone cavity and an impact cone protrusion. Wings spread out based upon the swelling of the gelatin seal and assist in the retention of the suture seal. U.S. Pat. No. 5,860,990 to Nobles et al. discloses a suturing device which includes sutures having needle points at terminal ends of the suture wire. The sutures are made of NITINOL memory shape metal material. When the memory shape metal is freed from the lumen of a needle, the needle points, at the terminal ends of the metal sutures, flare out laterally beyond the lumen of the needle and the needle points are captured by suture catches which are also laterally disposed outboard of the needle. The catches pull the needle points and draw in the sutures.

U.S. Pat. No. 4,744,364 to Kensey discloses a tubular body at the end of a suture thread which expands after being pushed out from the lumen of a delivery needle. In the lumen, the body is contracted or compressed. U.S. Pat. No. 4,741,330 to Hayhurst discloses an apparatus for anchoring cartilage. The anchor is deformed in the lumen of a delivery tube, is thereafter pushed from the tube and springs laterally outward upon exiting the tube.

U.S. Pat. No. 4,705,040 to Mueller et al. disclose a T-shaped bar, having a length of 0.25 inches, at the end of a suture. The bar is held in place by a melted ball of material at the terminal end of the suture.

OBJECTS OF THE INVENTION

It is an object of the present invention to provide a suture which can be self secured on a bodily structure, tissue, organ, bodily substructure or vascular vessel wall with a toggle at the terminal end of the suture.

It is another object of the present invention to provide a generally T-shaped toggle which latches on an interior or inboard surface of a bodily structure, tissue, organ, bodily substructure or vascular vessel wall thereby permitting the balance of the suture to be drawn in and wherein the toggle grasps the bodily structure, tissue, organ, bodily substructure or vascular vessel wall.

It is a further object of the present invention to provide a toggle configured as a bar at the end of a suture.

It is another object of the present invention to provide a metal wire suture with a T-shaped toggle or a toggle wire element attached to the terminal end of a suture wire.

It is a further object of the present invention to provide a suture and a suture toggle wherein the suture toggle includes a protruding leg or tab which is utilized by a needle delivery system to insert the suture toggle into the bodily structure, tissue, organ, bodily substructure or vascular vessel wall.

It is a further object of the present invention to provide a suture delivery system including a slotted needle, within which is seated the leg or tab of the suture toggle, which assists in the process of inserting the suture toggle into the bodily structure, tissue, organ, bodily substructure or vascular vessel wall.

It is another object of the present invention to provide a self-securing suture with a suture toggle which can be used for minimally invasive surgical techniques.

It is another object of the present invention to provide a suture delivery system capable of delivering one or more self-securing sutures with suture toggles and which can be used for minimally invasive surgical techniques.

It is a further object of the present invention to provide a suture delivery system capable of delivering and embedding sutures into a bodily structure, tissue, organ, bodily substructure or vascular vessel wall when access to the suture delivery site is limited to approaching the site at an acute angle.

It is a further object of the present invention to provide a suture delivery system and toggle sutures utilized in laposcopic procedures.

It is a further object of the present invention to provide a suture delivery system which can be safely used to embed sutures into a bodily structure, tissue, organ, bodily substructure or vascular vessel wall during minimally invasive surgical techniques.

It is a further object of the present invention to provide a suture delivery system which can be safely used to set sutures into a bodily structure, tissue, organ, bodily substructure or vascular vessel wall, and which provides the health care provider utilizing the system measured control over the insertion of the sutures into the aforementioned bodily area.

SUMMARY OF THE INVENTION

The suture delivery system utilizes two sutures. Each suture has a filament body and a toggle bar. The delivery system includes an elongated central tube with two needle retainer guides and a cam distally disposed on the central tube. The needles have piercing needle ends and each needle end carries a respective toggle bar for a suture disposed thereon. A movable member, longitudinally movably mounted on the central tube, is coupled to the needles. The needles are movably disposed in respective needle retainer guides. An actuator is coupled to the movable member such that when the actuator longitudinally moves the movable member over the central tube, the needles, initially captured by the needle retainer guides, extend outward such that the needle ends move over the cam. In a further embodiment, the actuator includes a first user actuation surface coupled to the movable member and the central tube includes a second user actuation surface which is generally static. In a further embodiment, a locking member disposed on the second user actuation surface can be secured to the first user actuation surface to lock the delivery device with the needles in an extended position. As a further enhancement, each needle end includes a slot to capture the respective toggle bar thereat and the needle retainer guide includes an aligned slot such that the toggle bar extends through the needle end slot and the needle retainer guide slot. The cam may take one of a variety of shapes. Essentially, the needle ends splay outward and forward, distally over the cam. In a preferred embodiment, the movable member is biased with respect to the central tube (that is, the first user actuation surface is biased with respect to the second user actuation surface) such that the delivery system is biased to place the needles in the proximal position and the needle ends are substantially captured in the needle retainer guides. In a further embodiment, the needle ends are longitudinally offset. In another embodiment, movable blades are disposed on the movable member, enabling the user to cut the suture threads during use of the suture delivery device. Another embodiment utilizes a flexible, elongated introducer at the distal end of the central tube. A method for embedding sutures in a vascular wall or other biological substructure is also included.

BRIEF DESCRIPTION OF THE DRAWINGS

Further objects and advantages of the present invention can be found in the detailed description of the preferred embodiments when taken in conjunction with the accompanying drawings in which:

FIGS. 1A and 1B diagrammatically illustrate a suture with a suture toggle;

FIGS. 2A and 2B diagrammatically illustrate a suture delivery needle with and without the suture toggle;

FIGS. 3A, 3B, 3C, 3D and 3E diagrammatically illustrate the insertion and deployment of the suture toggle and, more particularly, FIG. 3E generally diagrammatically illustrates the size relationship between the suture toggle and a typical large artery in a human body;

FIGS. 4A, 4B and 4C diagrammatically illustrate a suture delivery system needle, a suture toggle and a modified delivery system;

FIGS. 5A–5F diagrammatically illustrate various protruding legs, tabs and other elements protruding from the suture toggle which assist in deployment of the suture toggle in the bodily structure;

FIG. 6 diagrammatically illustrates a suture having two terminal ends and two suture toggles;

FIGS. 8A–8C diagrammatically illustrate other suture toggles;

FIGS. 9A–9D diagrammatically illustrate a suture delivery system with and without a suture toggle;

FIGS. 10A and 10B diagrammatically illustrate the deployment of the suture toggle illustrated in FIG. 8A;

FIGS. 14A and 14B diagrammatically illustrate one delivery system for the suture and suture toggle utilized in conjunction with minimally invasive surgery;

FIGS. 15A and 15B diagrammatically illustrate front and side views of the suture delivery needle;

FIGS. 16A, 16B and 16C diagrammatically illustrate various configurations of the needle retention body or structure;

FIG. 16D is a cross-sectional view of the delivery system from the perspective of section line 16D'–16D" in FIG. 14A;

FIG. 17 diagrammatically illustrates an arterial puncture site in a large artery in a human;

FIG. 19 diagrammatically illustrates an exploded view of the suture delivery system shown in FIG. 18;

FIGS. 20A, 20B, 20C and 20D diagrammatically illustrate cross sectional views of the delivery system shown in FIG. 19 from the perspective of the corresponding section lines in FIG. 19;

FIGS. 21A–21F diagrammatically illustrate various configurations of wire sutures and wire toggle elements;

FIGS. 22A–22D diagrammatically illustrate needle delivery systems for the wire suture toggles;

FIGS. 24A–24C diagrammatically illustrate major operational steps to deploy suture toggles during laproscopic surgery with the delivery system shown in FIG. 23A;

FIG. 26 diagrammatically illustrates another embodiment of a suture delivery system;

FIG. 27A diagrammatically illustrates a suture delivery needle with a slot at its piercing end;

FIG. 27B diagrammatically illustrates a needle retainer guide used to capture a suture delivery needle;

FIGS. 28A, 28B and 28C diagrammatically illustrate a suture delivery system positioned adjacent a vascular wall prior to delivery of the sutures, and, more particularly, FIGS. 28B and 28C generally diagrammatically illustrate a suture delivery system with offset needles;

FIGS. 35, 36, 37, 38 and 39 diagrammatically illustrate the proximal end of an alternative embodiment of the suture delivery system, and more particularly, FIG. 35 provides an exploded view and FIG. 36 a cross-sectional view of FIG. 37;

FIG. 38 is a cross-sectional, detail view of the proximal end of the alternative suture delivery system from the perspective of section line 38' in FIG. 37;

FIG. 39 is a partial side view of an alternative embodiment of the suture delivery device including a locking member.

DETAILED DESCRIPTION OF THE PREFERRED EMBODIMENTS

The present invention relates to self-securing sutures, that is, sutures having toggles at the suture's terminal end, and various suture delivery systems.

Figure 23A:
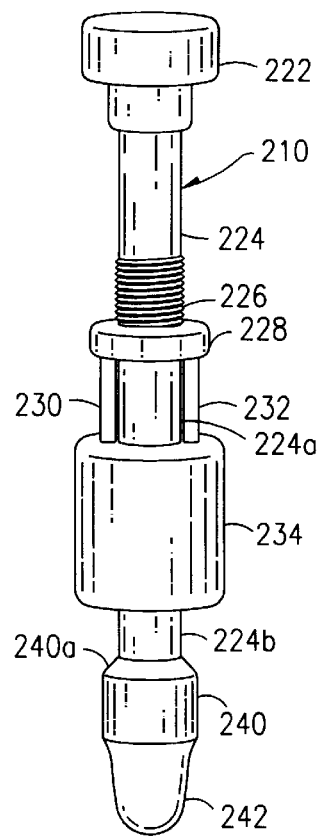
FIGS. 23A–23C diagrammatically illustrate a laproscopic device for the suture toggle delivery system and FIG. 23D is a cross-sectional view of a suture wire capture system (similar capture systems may be used with suture threads on the delivery systems in FIGS. 14A and 18)

FIGS. 1A, 1B, 2A and 2B diagrammatically illustrate sutures having toggles at the terminal end and a needle delivery system used in conjunction with the suture toggles. FIGS. 14A, 18, 28B, 31 and 34 diagrammatically illustrate simple delivery systems for the suture toggles. FIGS. 21A, B, C, D, E and F show wire suture toggles and FIG. 23A shows a delivery system for laproscopic surgery or other type of surgery wherein the surgeon seeks to suture fascia.

GENERAL PRINCIPLES

By utilizing the toggle principle, it is possible to enter the bodily structure, tissue, organ, bodily substructure or vascular vessel wall, and fix one end of a suture to the bodily structure, tissue, organ, bodily substructure or vascular vessel wall, without encircling the area. If two separate toggle sutures are fixed in this fashion, it becomes possible to tie those sutures with ease without the need for blind encirclement of the area in question. The increasing utilization of minimally invasive surgical techniques and arterial puncture site repair has created a need for improved methods of suture placement under adverse conditions of visibility and access.

The toggle principal lends itselfwell to the placement and fixation of sutures, ligaments, etc. In this approach, a suture or wire or other flexible attachment or closure device is passed through or into the tissue in a closed state. The "closed state" refers to the suture toggle deployed in the needle. Upon applying tension after the toggle leaves the needle tip, the toggle is positioned so that it cannot retrace the path through which it was applied or inserted by virtue of the fact that its shape and position will no longer allow egress from the bodily structure or tissue. Structures such as sutures or ligaments attached to the toggle are thereby fixed. One general embodiment of this invention consists of a T-shaped attachment to the end of a suture filament of either the same or different biocompatible material. The T bar is stiffer than the suture line, filament, thread or wire and offers significant resistance to extraction from the bodily structure once deployed. The suture toggle design in fine wire allows the insertion of the toggle, but restricts the egress from the tubular structure. With respect to wire sutures, provision is made for the applying or delivery device to secure both wires together and close the defect by shortening the wire by the simple, but effective, expedient means of twisting the instrument and its contained wires to secure them together. Provision is made to score the wires at the appropriate location so that the wires divide or separate upon twisting with a small, but secure, stub of twisted wire. In the alternative, a twisting and cutting instrument can be slid down the two opposing wires after the applicator is removed and the wires retained. This instrument would permit twisting and subsequent cutting of the wires in a blind procedure.

BASIC DETAILS OF OPERATION he applying device or delivery system consists of a small hollow core needle which allows it to be passed over a guide wire which has been retained at the puncture site. The delivery system contains two small hollow needles in opposition at just the right distance on either side of the guide wire and, thus, the puncture site. In another iteration, the needle can be solid with hollow small toggle suture ends fitted over the needle rather than through them. In the first design, the needles are designed to contain the toggles and the wire or sutures. When the instrument is slid over the guide wire and through the skin incision site of puncture it is advanced until it is against the vessel or structure sought to be closed by a suture. In the case of a vein or artery, a "flashback tube" can be utilized in advance of the needles to demonstrate that the instrument is in the proper position. In addition, the length and design of the "flashback tube" is such that it protects the far wall of the structure, preventing toggling of two walls simultaneously. The core or central tube can be utilized as a flashback tube, or the central tube can be solid with a flashback tube either incorporated internally or mounted onto its surface. The claims appended hereto are meant to cover this solid core tube feature. The restricted length of the hollow needles also protects opposite walls of the artery or vein. A slide moves the two needles distally and then advances the needles through the vessel or structure wall until the toggles are deposited in the blood vessel with their trailing suture filament or wire leading from the vessel. The hollow needle also acts as a flashback tube bilaterally. The shape of the toggle, as designed, prevents egress from the vessel and traction on the wire or suture "sets" the T of the toggle flush against or in the structure wall. The suture is then tied or the wire twisted as appropriate.

Different toggle designs are provided as shown in the accompanying drawings. In this fashion, puncture wounds or other defects may be easily closed utilizing simple and inexpensive devices. The cost of complicated closure devices has been a deterrent to the universal acceptance of these previous devices. The utilization of a simple, inexpensive disposable device should remove many of the impediments for universal useage. The concept of toggling sutures for closure is new, safe and simple to use.

In one of the embodiments presented here, fine, partially annealed wire sutures are utilized to simplify the process by permitting fastening by simple twisting of the wires by the instrument, instead of having to resort to complex methods of tying. Scoring the wires at the appropriate distance allows them to break with twisting at a predetermined location leaving only a small wire stump on top of the structure.

Any biocompatible material for the suture and suture toggle may be used such as stainless steel wire, nylon sutures, or other synthetic biocompatible material. The methods of tying the sutures may vary with the materials used, but the toggling principle remains the same.

FIGS. 1A and 1B diagrammatically illustrate a suture 10 having a suture thread or suture body 12, a terminal end 13 and a toggle 14. FIG. 1B shows a side view of suture toggle system 10. In the illustrated embodiment, toggle 14 is generally a solid rectangular shape having a length 1, a width w (FIG. 1B) and a depth d. The width w of the toggle 14 is substantially similar to the outside diameter of the suture thread 12 as shown in FIG. 1B. Toggle 14 has chamfered ends and edges, one of which is chamfer edge 15. This chamfer reduces sharp edges. Further, toggle 14 includes an extending leg 16 protruding outboard away from terminal end 13 of suture 12. Extending leg 16 defines, in combination with toggle body element 18, an open catch mouth 20 leading to a narrower throat 21. Mouth 20 has a gap size large enough to be captured by a slot in the delivery needle discussed later. Leg 16 protrudes in a direction opposite the attachment of suture 12 to toggle 14.

FIGS. 2A and 2B diagrammatically show a suture delivery system 8 which includes needle 24 having a lumen 26, a piercing terminal end 28 and an open ended slot 30. Open ended slot 30, sometimes called a needle toggle slot herein, is open at the piercing end segment 28 of needle 24. In the illustrated embodiment, piercing terminal end segment 28 (typically a sharp edge) of needle 24 is angularly disposed with respect to the axial center line of needle 24.

Toggle suture system 10 is shown as disposed in lumen 26 of needle 24 in FIG. 2B. Suture toggle 14, and particularly protruding leg 16, is adapted to seat within slot 30 of needle 24.

FIGS. 3A–3D diagrammatically illustrate basic operational characteristics of suture toggle system 10. Similar numerals designate similar items throughout all the drawings. In FIG. 3A, suture delivery system 8, consisting of needle 24 loaded with suture 12 and suture toggle 14, approaches a bodily structure, tissue or organ wall 31. As an example throughout the drawings (excepting drawings FIG. 24A–24C), reference will be made to arterial wall 31. However, any type of bodily structure, tissue, organ, bodily substructure or vascular vessel wall may be sutured using the suture toggle system 10 discussed herein. Wall 31 is representative of other bodily structures tissues and organs. Delivery system 8 approaches arterial wall 31 as shown by arrow 33. Piercing end 28 of needle 24 ultimately pierces and enters arterial wall 31.

FIG. 3B diagrammatically shows that needle 24 has fully entered and passed through arterial wall 31. At this point in time, blood flow is noted by a "flash" from the lumen 26 of needle 24. Other "flashback" systems may be utilized. See central tube 62 in FIG. 14A. This flash of blood provides a visual indication to the physician that the needle 24 has fully penetrated into the lumen of the artery or other structure.

In FIG. 3C, the physician is withdrawing needle 24 and protruding leg 16 of toggle 14 is caught on the inboard surface of arterial wall 31. In FIG. 3D, needle 24 is withdrawn from arterial wall 31 and toggle 14 and suture 12 is self secured in artery wall 31.

FIG. 3E diagrammatically illustrates the general proportional size relationship between artery wall 31, the artery in general, toggle 14 and suture 12. To further illustrate one proposed embodiment of the suture toggle, the following Exemplary Dimensional Table is provided.

| Exemplary Dimensional Table | |
|---|---|
| head length | 0.10–0.12 mm (approx.) |
| head depth | 0.020 mm (approx.) |
| OD suture | 3/0 nylon |
| suture length | 45 cm (approx.) |
| head width | 0.10–0.012 mm (approx.) |
| gap | 0.008 mm or more (approx.) |
| typical delivery needle | 0.028 mm OD (approx.) |
|  | 0.023 mm ID (approx.) |
|  | 21 gauge |
| large artery size | about 7 mm ID (approx.) |

FIG. 4A diagrammatically illustrates suture toggle 14 and suture thread 12 disposed in needle 24. Protruding leg 16 is also disposed in slot 30. However, suture thread 12A is disposed outside of needle lumen 26. This is accomplished by providing a secondary slot 34 within which passes suture thread A. Secondary slot 34 is sometimes referred to herein as a suture slot in the needle.

FIG. 4B diagrammatically shows open ended suture slot 34 at terminal end 29 of needle 24. Terminal end 29 of needle 24 is part of piercing terminal end 28. In the illustrated embodiment, suture slot 34 is opposite toggle slot 30 which retains, in a loaded mode, protruding leg 16 of suture toggle 14. The position of the suture slot relative to the toggle slot varies dependent upon the position of the protruding leg, tab, wire element or loop on the suture toggle.

FIG. 4C diagrammatically shows needle 24 within which is loaded suture toggle 14. Protruding leg 16 protrudes towards suture thread 12A. In this illustrated embodiment, slot 30 also operates as a suture slot. In addition, needle 24 includes rib 36 which enables the suture needle to be inserted into the blood vessel 31 by a pushing in action.

Figure 5G:
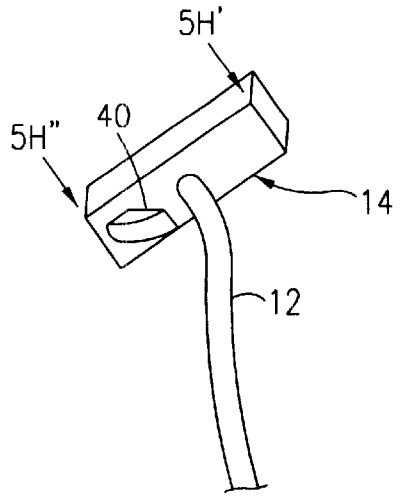
FIGS. 5G and 5H diagrammatically illustrate various suture toggles with depending tabs.

FIGS. 5A through 5H diagrammatically illustrate various modifications of suture toggle 14. FIG. 5A diagrammatically illustrates suture toggle 14 having a protruding leg 16 which protrudes outboard from the toggle opposite suture thread 12. Particularly, toggle 14 is a toggle bar. As used herein, the term "toggle" refers to a piece or a device for holding or securing suture thread 12. The term "toggle" also encompasses the concept that it is a cross piece attached to the end of suture thread 12 in order to prevent slipping or removal of the suture. The following Bar Shape Table provides some illustrative examples of the geometric shape of the toggle bar.

| Bar Shape Table |
|---|
| a straight piece of suture material which is longer than it is wide |
| rectangular |
| oblong |
| elliptical |
| an elongated cylinder |

As used herein, the term "bar" refers to a straight piece which is longer than it is wide. As shown in FIG. 5A, leg 16 is formed from a partially separated segment of toggle bar 14. Remaining segment 18 continues to form part of the toggle bar basic shape.

FIG. 5B shows a depending protruding leg 38 which protrudes inboard toward suture thread 12. Leg 38 is cut away or formed from toggle bar segment 39. Leg 38 is retained by and captured within open ended toggle slot 30 of needle 24. Gap 20 between leg 38 and toggle remainder section 39 is one of the important features.

FIG. 5C diagrammatically illustrates toggle suture 14 including a tab 40 depending from inboard surface 41 of suture toggle 14. Inboard surface 41 is integral with or attached to suture terminal end 13. Surface 41 is inboard with respect to suture filament or thread 12.

FIG. 5D diagrammatically shows tab 40 depending toward suture thread 12. FIG. 5D shows tab 40 consisting of either a solid triangular body, a finger or a conical body. The width of tab 40 is smaller than suture toggle 14. Protruding tab 40 has a raised terminal edge 42, see FIG. 5E, which faces away from suture thread 12. Tab 40 coacts with open ended slot 30 of suture delivery needle 24 (see for example FIG. 4B). The tab fits in toggle slot 30. In a different embodiment, suture slot may be placed 90 degrees from toggle slot 30 (see FIG. 9C) to provide clearance of the tab from the thread during withdrawal of needle 24.

FIG. 5F diagrammatically illustrates suture toggle 14 carrying two tabs 40, 43 depending from inboard surface 41 of suture tab 14.

FIG. 5G diagrammatically shows tab 40 as a solid triangular body. Suture toggle 14 is also a solid rectangular body without chamfered edges.

Figure 5H:
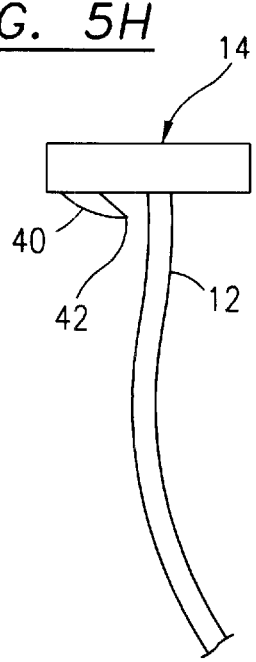

FIG. 5H diagrammatically illustrates suture toggle 14 from the perspective of section line 5H'–5H" in FIG. 5G. Tab 40 has a raised terminal edge 42 which faces towards suture thread 14. Accordingly, the tab can either face away from suture thread 12 as in FIG. 5E or towards suture thread 12 as in FIG. 5H.

FIG. 6 diagrammatically shows suture toggles 14 and 14a disposed at opposite terminal ends of suture thread 12. Suture thread 12 has a length is which is, in one embodiment, about 16–18 inches. FIG. 6 also shows that suture toggle 14 has been deployed beneath body layer 31.

Figure 7:
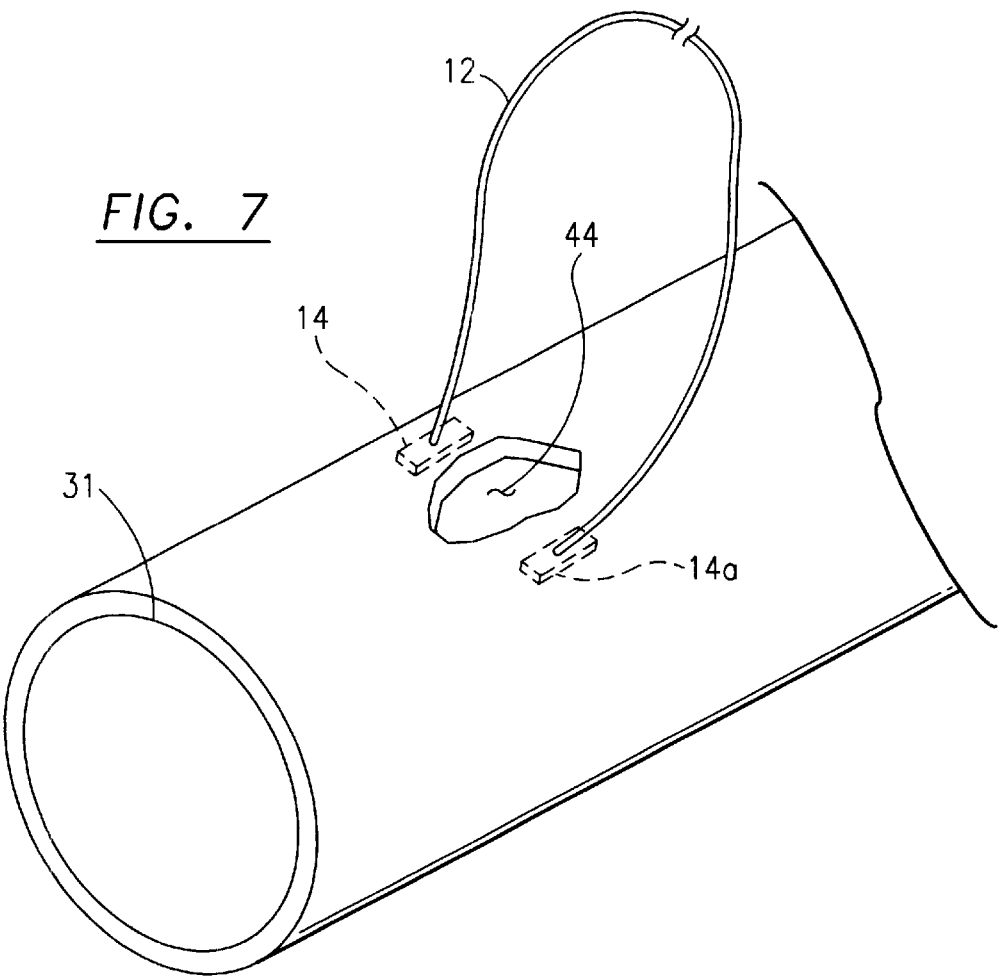
FIG. 7 diagrammatically illustrates a suture with two suture toggles, at both terminal ends of a suture thread, deployed about an arterial puncture site.

FIG. 7 diagrammatically shows deployed suture toggles 14 and 14a on blood vessel wall 31. The suture toggles are deployed beneath arterial wall 31. Arterial wall 31 is illustrated as having arterial puncture site 44. Suture toggles tabs 14, 14a are deployed on either side of puncture side 44. Suture thread 12 connects suture toggles 14, 14a. In operation, the surgeon or physician ties off suture thread 12 thereby closing arterial puncture site 44.

FIGS. 8A, 8B and 8C diagrammatically illustrate suture toggle 14 with a protruding leg 16 along one side. Particularly, FIG. 8A diagrammatically shows suture toggle 14 as a toggle bar with chamfers along its side edges. One of the chamfers is identified as chamfer 15. A protruding leg 16 is formed by partly separating toggle 14 from remaining toggle segment 18. This creates an open mouth 20 which is disposed in the toggle slot in needle 30. See FIG. 2A.

FIG. 8B shows a top view of suture toggle 14 and clearly shows that protruding and extending leg 16 is formed by partially separating leg 16 from the remaining toggle body portion 18.

The generally solid body rectangular toggle bar 14 has sides 2, 3, 4 and 5 which are generally in parallel planes with respect to the axial centerline of suture thread 12 if the thread were laid out straight. Items protruding from toggle bar walls 2, 3, 4, 5 are normal (perpendicular) to the suture thread.

FIG. 8C shows a toggle end view and toggle mouth 20.

FIGS. 9A–9D show needle 24 with and without a retained toggle suture. FIG. 9A shows toggle slot 30 in needle 24 located approximately midway along piercing terminal edge 28 of needle 24. The toggle slot can be re-positioned dependent upon the size of the suture, the leg or tab, and the item to be sutured. FIG. 9B also shows toggle slot 30 of needle 24 approximately midway along needle piercing edge 28. FIG. 9B also shows suture toggle 14 deployed in toggle slot 30. Suture thread 12 runs or passes through the lumen 26 of needle 24.

In FIG. 9B, slot 30 retains protruding leg 16 which protrudes from side edge 5 of the toggle bar. The side edge protruding leg 16 is shown in FIGS. 8A–8C. Leg 16 protrudes normal or perpendicular to suture thread 12.

FIG. 9C shows needle 24 having toggle slot 30 and suture thread slot 34. Suture thread slot 34 is formed or created approximately 90 degrees from toggle slot 30.

FIG. 9D shows suture toggle 14 with a side end protruding leg 16 wherein suture thread 12 runs through suture slot 34 of needle 24.

FIG. 10A shows suture toggle 14 deployed in arterial wall 31.

FIG. 10B is a detailed view showing suture toggle 14 deployed on an inboard surface of arterial wall 31. Currently, it is believed that the toggle bar with a leg or tab protruding from bar side 2, 3, 4 and 5 is preferable.

FIG. 8B shows toggle bar 14 with side surfaces 2, 3, 4 and 5. It is currently believed that a tab or leg protruding from one of the side surfaces is better suited than an outboard extending tab or leg (see FIG. 5A) or a depending tab or leg (see FIG. 5B). The depending leg or the depending tab may injure an arterial 31 in certain situations. When toggle anchoring is required, the depending leg or wire is preferred. An upstanding or outboard tab or leg may impede blood flow. However, in some applications, these tab-leg configurations may be beneficial if it achieves better attachment by the suture toggle on the body structure, tissue or organ. A side leg or tab is currently thought to be better than an outboard leg or tab (see outboard leg 16 in FIG. 1A) because an outboard protruding leg or tab may further complicate and impede blood flow or fluid flow through the bodily structure, tissue or organ, particularly if the structure is an artery or a vein.

Figure 11A:
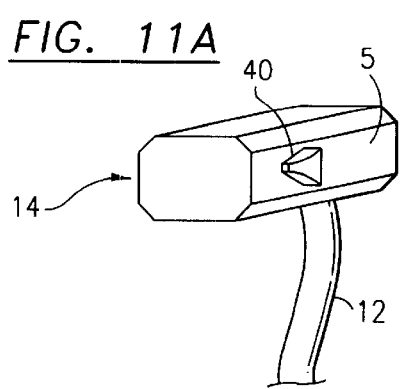
FIGS. 11A, 11B and 11C diagrammatically illustrate other types of tabs protruding from suture toggles.

FIG. 11A diagrammatically shows suture toggle 14 having a protruding tab 40 protruding from side surface 5 of the toggle bar.

Figure 11B:
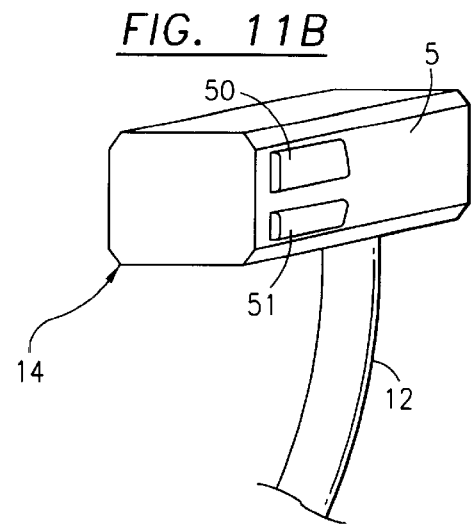
Figure 11C:
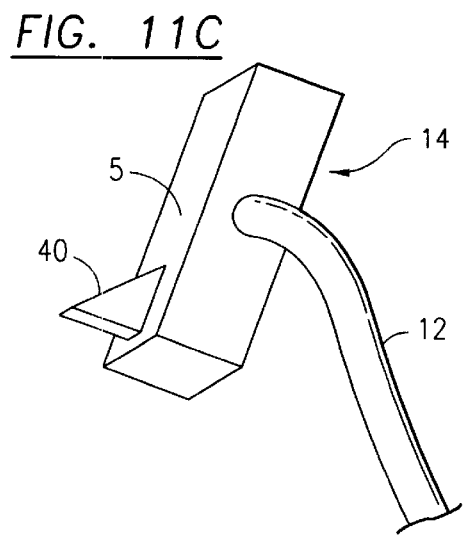

FIG. 11B shows protruding legs or arms 50, 51 protruding from side surface 5 of toggle bar 14. A plurality of legs or tabs may be utilized. FIG. 11C shows toggle 14 with a generally planar triangular tab 40 protruding from side face 5. Tab 40 in FIG. 11A is generally conical in structure with squared off surfaces. Tab 40 in FIG. 11C is generally a planar triangle.

Figure 12:
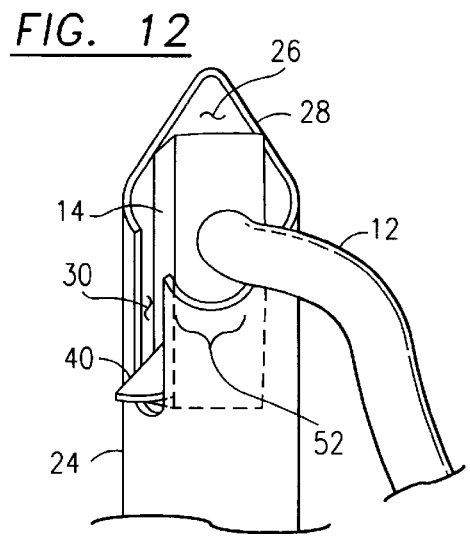
FIG. 12 diagrammatically illustrates a suture toggle deployed in a suture delivery needle.

FIG. 12 shows suture toggle 14 with a triangular tab deployed within the lumen of delivery needle 24. Tab 40 of toggle 14 protrudes from toggle slot 30. Suture 12 is deployed such that it exits lumen 26 of needle 24 near proximal edge region 52 of piercing terminal edge 28 of needle 24. Proximal region 52 may be rounded or smoothed to avoid cutting suture thread 12.

Figure 13A:
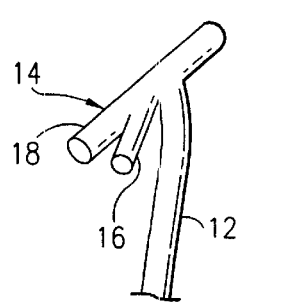
FIGS. 13A and 13B diagrammatically illustrate a suture toggle configured as a cylinder with a protruding side leg.
Figure 13B:
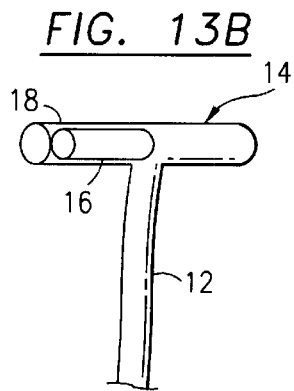

FIG. 13A and 13B diagrammatically illustrate suture toggle 14 configured as a cylindrical bar with a laterally protruding leg 16. Leg 16 is also cylindrically shaped and protrudes laterally from toggle bar element 18. Leg 16 is generally normal to suture thread 12. Leg 16 is not cut from or separated from the cylindrical toggle bar.

Figure 13C:
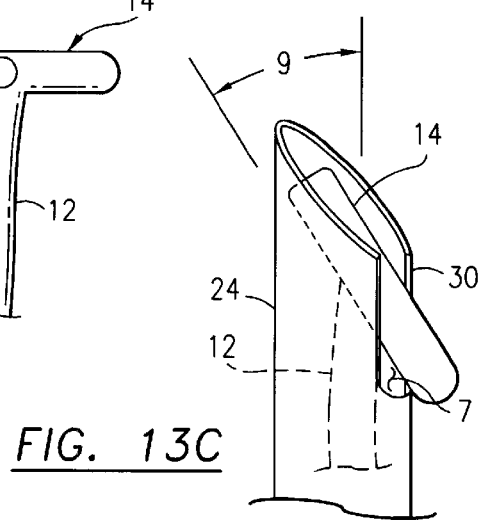
FIG. 13C diagrammatically illustrates a suture toggle configured as an angled T-bar deployed in a needle.

FIG. 13C diagrammatically illustrates toggle bar 14 at an angle 9 with respect to the axial centerline of suture thread 12. In this configuration, the acute angle 7 between angled toggle bar 14 and suture thread 12 is disposed within suture slot 30 of needle 24. This angulated configuration may enable long T-shaped bar deployment in needle 24. The term "long T-shaped" refers to the length of sides 3,5 (see FIG. 8B) relative to the cross-sectional dimension of suture thread 12. This implementation may also avoid the use of protruding legs, tabs or members.

FIGS. 14–20 diagrammatically illustrate various suture delivery systems.

FIG. 14A diagrammatically shows suture delivery system 60 which includes a basic or central tube 62 which runs over a guide wire 64. Guide wire 64 typically is not part of the suture delivery system. The illustrated delivery system in FIG. 14A is used to close puncture wounds made during catheterization. Guide wires 64 are used during such medical procedures. For purposes of explanation, suture delivery needles 66, 68 carry suture toggles and suture threads generally shown and discussed earlier in connection with FIGS. 1–13.

FIG. 15A shows suture needle 66 having a piercing edge 67 and a toggle slot 69. FIG. 15B diagrammatically illustrates a side view of suture needle 66.

Returning to FIG. 14A, base tube 62 rides over guide wire 64 in order to properly place suture needles 66, 68 on either side of arterial puncture 44 shown in FIG. 7. Suture needles 66, 68 have piercing ends 67, 67a which are laterally deployed a distance 69 from base central tube 62. In this suture delivery system, suture needles 66, 68 are made of metal having a shape memory such that when needle end segment 70 is free from needle containment or retaining structure 72, the distal ends of needles 66, 68 spring laterally outward a distance 69.

Needles 66, 68 run and protrude through needle retainer body 72 and also protrude proximally from proximal end 74 of retainer 72 towards thumb nut set 76. Proximal needle ends 75, 77 for needles 66, 68 are generally near thumb nut set 78.

Needle retention structure 72 has a proximal tube member 80 such that tube 80 runs over central tube 62. The operator moves needle retainer structure 72 by moving thumb nut set 78 in the direction shown by arrow 82. As shown in FIG. 16D, proximal tube 80 (attached to needle retainer body 72) has longitudinal slots 73a, 73b. Needles 66, 68 are attached to base or center tube 62. Hence, when tube 62 is stationary and needle retainer 72 is moved, needles 66, 68 are either exposed (FIG. 14A) or fully retained and covered (FIG. 14B).

FIG. 14B shows that needle retaining structure 72 has been pushed forward such that proximal ends 75, 77 of needles 66, 68 are proximate or near thumb nut set 78. Piercing edges 67, 67a are disposed at, near or below distal edges 79, 81 of needle retention structure 72. When the structure delivery system 60 is placed on guide wire 64 and placed near arterial puncture site 44 (FIG. 17), thumb nut set 78 (mounted on tab 80 and retainer 72) is then withdrawn in a direction opposite arrow 82 in FIG. 14A, and distal end 70 of needles 66, 68 are then exposed and sprung laterally outward due to the memory shape of the needles. The surgeon then places the distal end of tube 62 into arterial puncture 44 (FIG. 17) and continues to move delivery system 60 down guide wire 64 until he or she sees a flash of blood when piercing ends 67, 67a of needles 66, 68 pierce arterial wall 31. A flashback may also occur through base tube 62. Toggle insertion generally occurs at sites 83, 85 (FIG. 17). The surgeon then withdraws the needles thereby leaving the toggle ends of the sutures on the inside arterial wall 31. The surgeon can then close the arterial puncture after removal of guide wire 64 in a manner described above in connection with FIG. 7.

FIGS. 16A, 16B and 16C show different structures for needle retention structure 72. In FIG. 16A, retention structure 72 is generally circular in configuration. The structure contains left and right passages 82, 84 within which pass needles 66, 68. A central passage 86 permits passage of base tube 62.

FIG. 16B, needle retention structure 72 is elliptical or oblong. In FIG. 16C, needle retention structure 72 includes a central cylindrical body 88 and two side bodies 90, 92. Side body 90 has a lumen through which passes needle 66. Side body 92 includes a lumen through which passes needle 68. Central body 88 includes a lumen through passes central or base tube 62.

FIG. 17 shows that a typical size of the large artery having dimension da which is approximately 7 mm (inside diameter) and puncture site 44 has an approximate opening size ap of approximately 2–3 mm. The lateral distance between respective piercing edges 37, 37a of needles 66, 68 is approximately 5–6 mm. The lumen of the suture toggle delivery needles 66, 68 is approximately 0.02 mm. Accordingly, the puncture for the suture toggles is small compared with the size of the arterial puncture which in turn is smaller than the inside diameter da of large artery 31.

Figure 18:
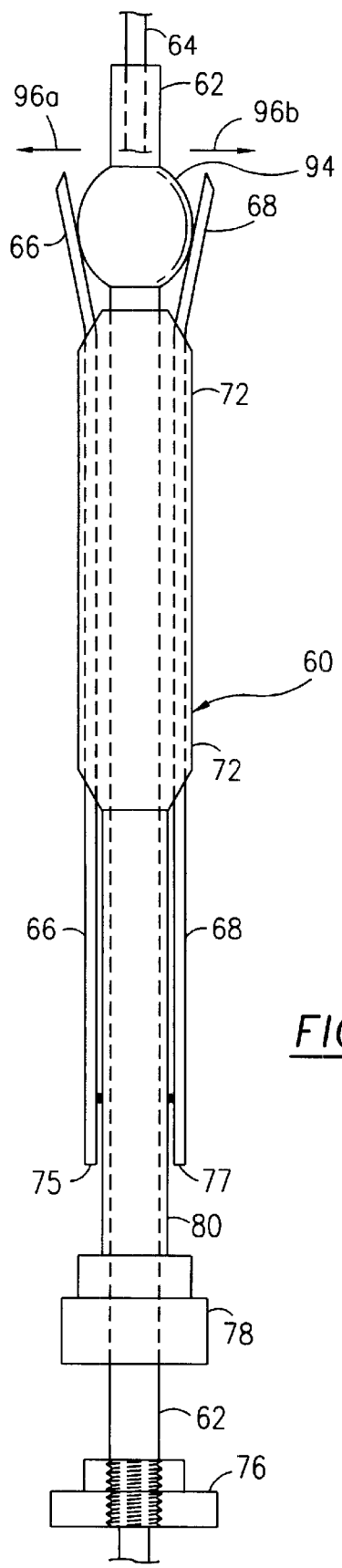
FIG. 18 diagrammatically illustrates another type of suture delivery system.

FIG. 18 diagrammatically shows delivery system 60 including a shaped element 94 which forces needles 66, 68 to move laterally in the direction of arrows 96a and 96b outboard and away from central tube 62. Shape element 94 acts as a cam surface and needles 66, 68 follow the proximal cam surface of the shape 94. The proximal end segments of needles 66, 68 are attached to outer tube 80 which is further attached to screw set 78. When outer tube 80 moves forward and aft over central tube 62, the distal ends of needles 66, 68 move forward and aft over cam shape surface 94. Cam shape element 94 is mounted on central base tube 62. The following Needle Delivery Flare Table describes some shapes of the cam shape 94.

Needle Delivery Flare Table ball, spherical
olive
oblong
frustoconical, convex frustoconical, concave frustoconical
triangular
conical
angled ribs (with apex at a proximal end)
distally truncated, continuously curved FIG. 19 diagrammatically shows an exploded view of delivery system 60. Thumb screw set 78 is attached to the proximal end of needle carrying tube 80. Needles 68, 68 are attached to carrying tube 80.

FIG. 20A shows needles 66, 68 from the perspective of section line 20A'–20A" in FIG. 19. The attachment of needles 66, 68 to needle carrying tube 80 is shown in a cross-sectional view in FIG. 20B from the perspective of section line 20B'–20B" in FIG. 19. The lumen 80a of needle carrying tube 80 is large enough to accommodate central tube 62. Central tube 62 extends through needle carrier tube 80.

Needles 66, 68 and needle carrying tube 80 are placed over central or base tube 62. Guide wire 64 extends through lumen 63 of central tube 62 when the system is deployed and in use.

FIG. 20C shows a cross-sectional view of central tube 62 from the perspective of section line 20C'–20C" in FIG. 19. Needle retention body 72 is mounted on central tube 62.

Needle retention body or structure 72 is mounted on central tube 62. A cross-sectional view of one embodiment of needle retention body 72 is shown in FIG. 20D. FIG. 20D is a view from section lines 20D'–20D" in FIG. 19. Needle cam shape 94 is attached to the distal end of central tube 62 slightly beyond needle exit ports 98, 99 of needle retention body 72. It should be noted that needle retention body 72 may take one or more of the shapes illustrated above in connection with FIGS. 16A, 16B and 16C.

To construct the delivery system shown in FIG. 19, needle carrying tube 80 and needles 66, 68 are placed over central tube 62. Needles 66, 68 are fed into needle entrance ports 97a, 97b. Needles 66, 68 are placed into the left and right side needle lumens of needle retention structure 72 until they are proximate needle exit ports 98, 99. Thereafter, thumb nut set 76 is placed on the proximal end of central tube 62 by an appropriate attachment means (e.g., a thread). Accordingly, face 101 of set 76, along section lines 102'–102," is near or adjacent face 103 of set 78 at section lines 104'–104" which is the proximal end of thumb nut set 78. In a preferred embodiment, thumb nut set 78 may cooperate with thumb nut set 76 to lock the needle delivery system and suture delivery system together prior to deploying the system on guide wire 64. After deployment, the system takes the configuration shown above in connection with FIG. 14B except central tube 62 includes a needle cam shape 94. This cam shape is absent from FIG. 14B.

At the time of suture toggle deployment, needle carrying tube 80 is moved distally while central tube 62 remains stationary thereby causing needles 66, 68 to leave exit ports 98, 99 and move over needle cam surface shape 94. At that time, the distal ends of needles 66, 68 move laterally outboard (relative to the axial center line) in the direction shown by arrows 96a, 96b in FIG. 18 until the piercing surfaces of needles 66, 68 are distally beyond the needle cam shape 94. At that time, the operator inserts the distal end of central tube 62 into arterial puncture 44 shown in FIG. 17. Thereafter, needles 66, 68 pierce arterial wall 31, deposit the toggles in the artery's lumen and at the underside of arterial wall 31 and the operator withdraws the needles by moving thumb nut set 68 proximally with respect to central tube 62 which is preferably held stationary. This causes needles 66, 68 to withdraw and laterally collapse since cam surface shape 94 no longer forces the distal end of the needles to protrude laterally outward beyond central tube 62. The needles are also drawn into needle retention body 72. When the needles' terminal ends are at or near exit ports 98, 99, the entire delivery system is withdrawn and the surgeon or physician ties off the suture wire as shown in FIG. 7.

FIGS. 21–22 diagrammatically illustrate a toggle suture made of wire. This wire may be stainless steel wire. The toggle may also be memory shape metal. In contrast, the sutures discussed above in connection with FIGS. 1–13 are made of nylon or other synthetic biocompatible material.

FIG. 21A shows suture wire 110 having a wire element toggle 114 at suture terminal end 113. The wire is typically stainless steel but may be an other type of biocompatible metal material. Wire element toggle 114 includes a double strand segment 116. Wire element toggle 114 is angularly disposed, that is, disposed over angle 118a with respect to the axial central line of suture wire 110. In addition, wire element toggle 114 includes a depending wire tip section 118.

FIG. 21B shows wire element toggle 114 disposed on an inboard side of body structure, tissue or organ layer 31. Depending wire element 118 protrudes into body layer 31 thereby locking or anchoring the toggle suture in place.

FIG. 21C shows wire suture 110 with a wire element toggle 114 being normal with respect to the suture wire. The angular disposition of toggle 114 to the axial centerline of laid-out suture wire 110 is related to the needle delivery system and the spring action and toggle or latch action of the suture toggle.

FIG. 21D shows that depending leg 118 is angularly disposed at angle 121 with respect to the central axis of wire element toggle 114. The angular position is related to the needle delivery system and the degree of locking necessary on bodily structure 31.

FIG. 21E shows suture wire 110 having a wire body 122 (about 16"–18") and having toggle elements 114a, 114b attached to suture terminal ends 113a, 113b.

FIG. 21F shows wire element toggle 114 attached by welding or other type of mounting mechanism to suture terminal end 113.

FIG. 22A shows needle delivery system 124 which retains wire element toggle 114 and wire suture 112. Toggle element 114 includes an open loop 135 and a linear segment 136. Linear segment 136 rests against the proximal end wall of a needle slot 130. Open loop toggles are shown FIGS. 21E, 22A, C and D.

FIG. 22B shows needle 124 having a toggle needle slot 130 and wire element toggle 114 having a depending leg 118 resting on toggle needle slot 130. Suture wire 110 is disposed in lumen 126 of needle 124. Leg 118 is used to mount suture wire 110 in the delivery needle. Legs 119 are shown in FIGS. 21A, 21B, 21D and 21F.

FIG. 22C shows toggle element 114 with open loop 135 disposed in toggle needle slot 130.

FIG. 22D shows wire element toggle 114 in toggle slot 130 of needle 124. Needle 124 also includes a suture slot 134 through which runs wire suture 110. Wire element toggle 114 is retained within toggle slot 130 via its open loop. The operation of the wire suture and wire element toggle is substantially similar to the suture toggle discussed above in connection with FIGS. 1–13. The operation and deployment of the suture toggle and the suture needle is also similar to that discussed above in connection with FIGS. 1–13.

Figure 23B:
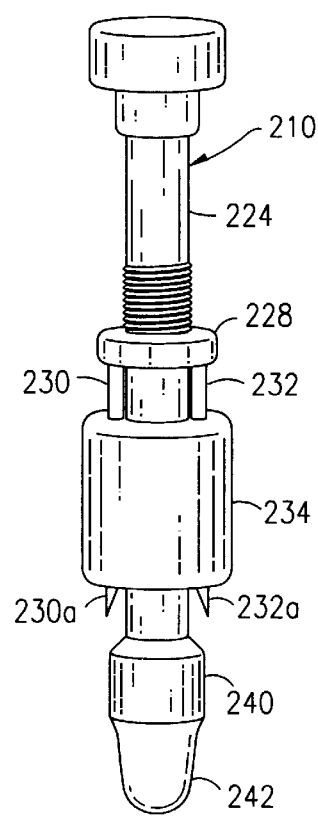
Figure 23C:
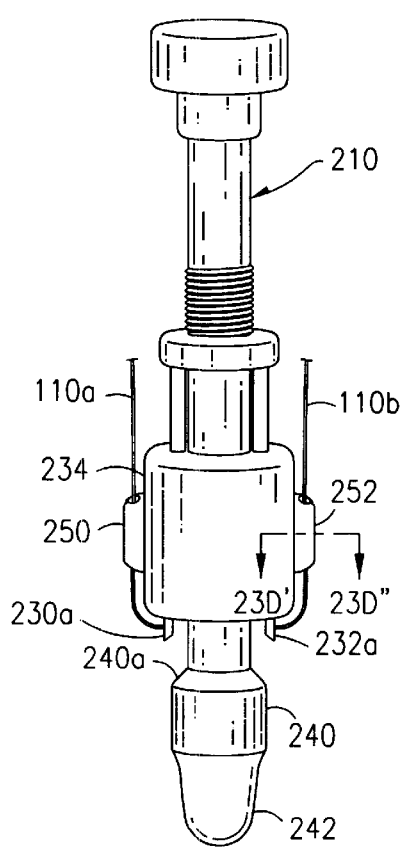

FIGS. 23A, 23B and 23C diagrammatically show a delivery system 210 used in connection with fascia 220 to deploy suture toggles in a manner discussed above in connection with FIGS. 1–13 and 21–22. The deployment device shown and described in connection with FIGS. 23–24 is typically used in laproscopic surgery. However, it maybe used whenever a surgeon needs to suture fascia.

Delivery system 210 includes handle 222 and central tube 224 which carries thread 226 at its distal end. Thread 226 coacts with threads on an inboard surface of collar 228. Collar 228 is attached to suture needles 230, 232. Suture needles 230, 232 move within needle passages in needle retention body 234. This mechanical theory and feature is generally discussed above in connection with needle retention body 72 and FIGS. 14A and 18.

Central body or tube 224 has a mid-section 224a and a distal section 224b. The distal end of distal section 224b is a bulbous terminal including a radially large fascia lift element 240 and a plunge cone 242. A plunge cone 242 is mounted to the distal end of enlarged lift segment 240.

Fascia is lifted by the proxial, peripheral radial lip 240a of lift element 240.

FIG. 23B diagrammatically shows an operational state of delivery system 210. The distal ends 230a, 232a of needles 230, 232 protrude axially beyond the distal end of needle retainer 234. In operation, the suture toggles are deposited in the fascia by rotational movement of body 224 to collar 228 translated into axial movement and needle ends 230a, 232a are withdrawn by counter rotation of central tube 224 thereby moving collar 228 in a proximal direction. Withdraw of the suture needles causes the suture toggles to remain embedded in the fascia.

FIG. 23C shows a delivery system 210 with suture wires 110a, 110b disposed outboard of suture needle ends 230a, 232a. The suture wires are run through capture channels 250, 252 on either side of needle retention body 234.

Figure 23D:
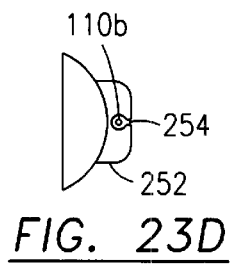

FIG. 23D is a diagrammatic cross-sectional view from the perspective of section lines 23D'–23D" in FIG. 23C. Suture capture body 252 captures suture wire 110b in a channel 254. Upon deployment of the toggle suture in the fascia, the physician simply moves the suture wire outboard of the channel 254 and closes the site.

FIGS. 24A, 24B and 24C diagrammatically illustrate the operation of delivery system 210. In FIG. 24A, cone 242 and fascia support or lift element 240 have been inserted into a hole or cavity formed in fascia 220. The surgeon or physician allows the fascia to rest thereby closing the hole about distal cental rod segment 224b.

In FIG. 24B, the physician gently raises delivery system 210 in the direction shown by arrow 275. Lift element lip 240a causes fascia 220 to rise thereby lifting fascia 220 above underlying tissue elements 220a. Further, the physician rotates central handle 224 with respect to collar 228 thereby causing suture needles 230a, 232a to protrude beyond the distal end of needle retention body 234.

In FIG. 24C, the physician has completely rotated handle 224 thereby completely deploying needle ends 230a, 232a through fascia 220. Upon complete deployment of the toggle carrying sutures, the suture toggles engage the inboard edge or side of fascia 220 preferably in the interstitial space between underlying material 220a. The toggles are caught by the fascia, leave the toggle carrying needles, latch onto the inboard surface of fascia 220 and remain in the fascia. The surgeon then counter rotates handle 224 with respect to collar 228 thereby withdrawing suture needle ends 230a, 232a from fascia 220. Essentially, needles 230, 232 are withdrawn and recaptured by needle retention body 234. The surgeon then gently withdraws fascia lift element 240 from fascia 220. The toggles are embedded in the inboard surface of the fascia and the surgeon can then close the fascia.

Figure 25A:
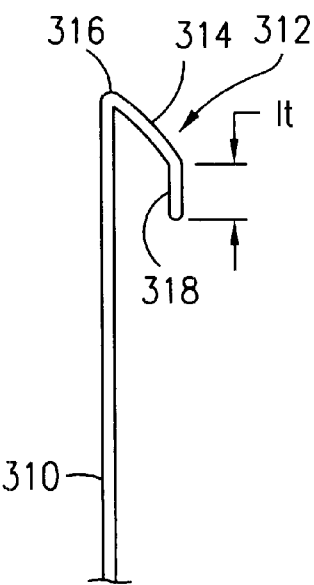
FIGS. 25A, B, C and D diagrammatically illustrate a hooked wire suture.

FIGS. 25A, B, C and D diagrammatically illustrate a wire toggle with a wire suture 310 and a wire toggle element 312. Toggle element 312 is configured as a hook with a crook or bend element 316 (0.008 or greater), an angled body segment 314 and an end segment 318. End segment 318 is generally in a plane parallel with respect to the axial centerline of wire suture 310 assuming the suture is laid out straight. The length It of hook end 318 is approximately 0.04. This configuration locks onto the inboard surface of the bodily structure after the wire suture is deployed beneath the surface. See generally FIG. 25D.

Figure 25B:
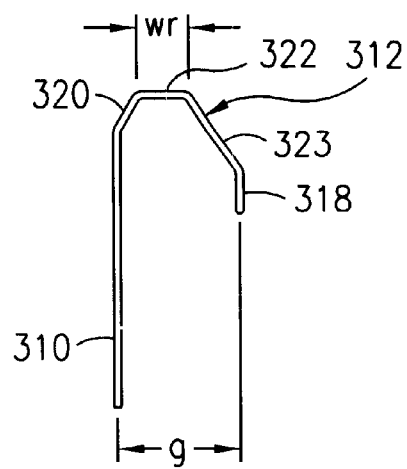
Figure 25C:
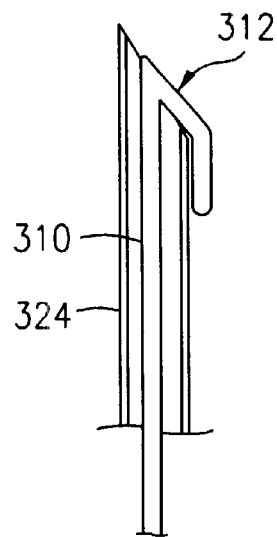

FIG. 25B illustrates toggle wire element 312 with a stepped radius or curve consisting of proximal angled segment 320, normal segment 322 (having a running length wr of about 0.020) and angled segment 323. Hook span g from suture 310 to end segment 318 is about 0.60. FIG. 25C shows hooked toggle 312 deployed in a delivery needle 324. In the illustrated embodiment, the needle does not have a suture slot.

Figure 25D:
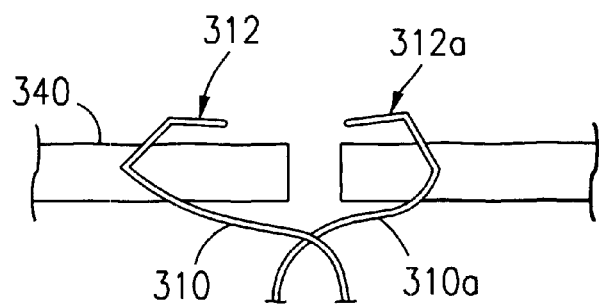

FIG. 25D illustrates the deployment of hook toggles 312, 312a and the integral or attached wire sutures 310, 310a twisted or crossed. In the configuration, the wire sutures are enabled to close the illustrated gap in body structure 340.

Delivery system 60 diagrammatically illustrated in FIGS. 26 through 40 operates substantially similar to delivery system 60 diagrammatically illustrated in FIGS. 18 and 19. FIGS. 26, 28A, 28B, 28C, 31 and 34 show delivery system 60 including an outboard protrusion or shaped element 94 which forces needles 66 and 68 to move laterally in the direction of arrows 330a and 330b in FIG. 29A outboard and away from central tube 62. The operation of delivery system 60 is also diagrammatically illustrated in FIG. 18.

FIG. 26 diagrammatically illustrates delivery system 60. Two sutures are loaded into respective needles with toggle bars 340a and 340b protruding from the corresponding needle ends and the adjacent needle retainer guides 342a and 342b. The needle retainer guides 342a, 342b are part of a needle retainer or structure 72 as illustrated in FIG. 18. FIG. 26 diagrammatically illustrates needles 66 and 68 substantially longitudinally covered by the needle retainer guides 342a and 342b and, at their proximal ends, the needles 66, 68 are captured within the proximal end of the guides. FIG. 26 also illustrates corresponding suture filament or suture thread bodies 350a and 350b extending outboard of the proximal end of system 60.

Delivery system 60 includes an actuator consisting of a static actuation unit with user actuation surfaces 360a and 360b forming loop handles or loop-shaped finger grips attached to the central tube 62. Loop handles 360a, 360b permit an operator to hold the delivery system 60 stationary relative to the suture delivery site. The system 60 includes a second, dynamic actuator with a user actuation surface 362. User actuation surface 362 is formed as a loop handle or loop-shaped finger grip attached to a movable member 80. Movable member 80 is also diagrammatically illustrated in FIG. 18. In both FIGS. 18 and 26, the movable member 80 is connected to needles 66 and 68. The delivery system 60 in FIG. 26 operates substantially similar to delivery system 60 in FIG. 18 with the added feature of having user actuation surfaces 360a, 360b and 362 to provide stability and measured control of the movement of needles 66 and 68 over cam 94. Cam 94 is mounted to stationary central tube 62. Static actuator with its user actuation surfaces 360a, 360b, central tube 62, central tube 62, needle retainer 72 and guides 342a, 342b, form a stationary body relative to movable member 80, attached needles 66, 68, and dynamic actuator element 362. Movable member 80, needles 66, 68, and user actuation surface 362 move with respect to the static elements.

FIG. 27A is an enlarged view of one delivery needle 66. The needles can be hollow. A suture filament body (not shown) runs within the lumen of each needle. Otherwise, the needle may be solid with a hollow tip, permitting the toggle bar to be loaded as diagrammatically illustrated in FIGS. 4A, 9D and 12. FIG. 27A diagrammatically illustrates a piercing needle end including a needle slot 30 which captures a toggle bar thereat.

Figure 29A:
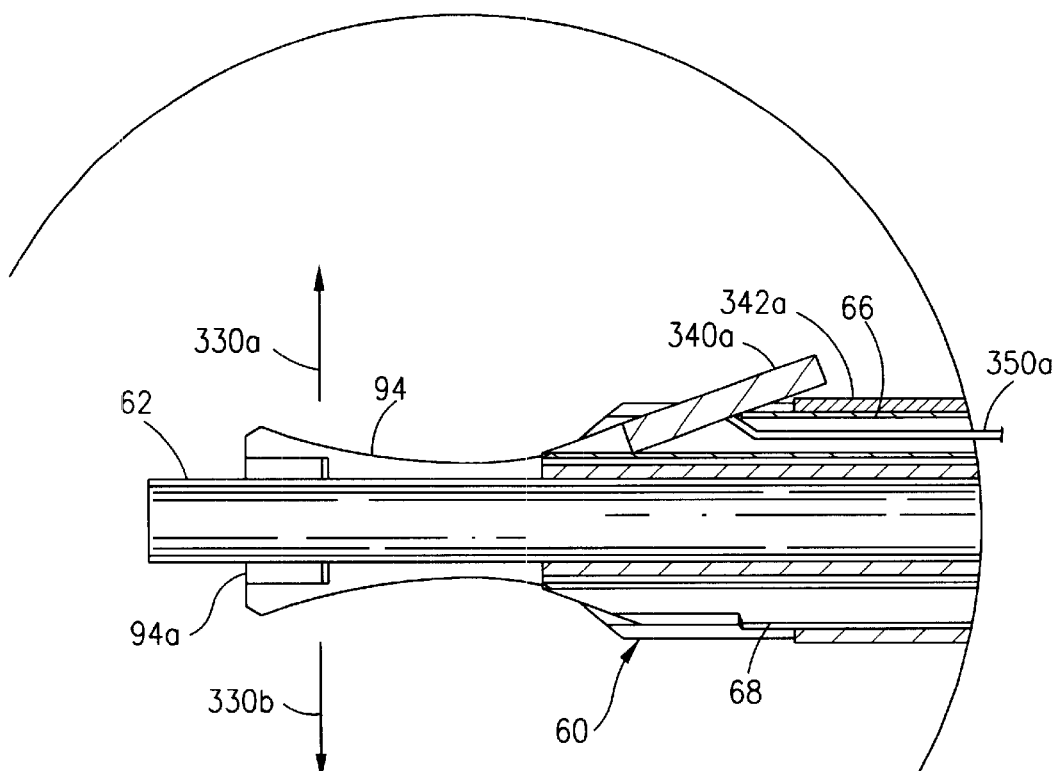
FIG. 29A diagrammatically illustrates an enlarged cross-sectional view of the delivery end or distal end of the suture delivery system with its suture delivery needles retracted and shows one needle with a suture and toggle bar disposed thereat.

FIG. 27B diagrammatically illustrates an enlarged view of one channel or needle retainer guide 342a. The needle guide directs the needle during its distally outward movement from the channel or guide end 343 towards cam 94 (see FIG. 26). FIG. 27B diagrammatically illustrates a respective needle retainer guide 342a with a slot 345. The slot 345 is primarily a safety feature which permits the piercing needle end 67 to be substantially contained within the needle retainer guide 342a prior to delivery of the suture. The slot 345 on the needle retainer guide 342a permits the portion of a toggle bar 340a (FIG. 26) protruding from a respective loaded needle end 67 to also protrude through the corresponding retainer guide slot 345 prior to delivery of the suture such that the respective piercing needle end 67 is not exposed. This captured needle end is depicted in FIG. 29A. The cooperation of slot 345 on needle guide 342a and toggle 340a and needle 66 is shown in FIG. 29A. Needle slot 30 is aligned with guide slot 345 to provide a compact structure when toggle 340a (FIG. 29A) is in these slots.

FIGS. 28A, 28B and 28C diagrammatically illustrate suture delivery system 60 positioned adjacent to a vascular wall 31 prior to delivery of the sutures. FIG. 28B diagrammatically illustrates delivery system 60 at angle 380 with respect to the vascular wall 31. Delivery of sutures under circumstances in which the delivery system can only be inserted at such an angle with respect to the longitudinal axis of the vascular vessel can be accomplished by staggering or longitudinally offsetting needles 66 and 68. Staggering causes one needle end to protrude further outward during delivery of the sutures than does the other needle end, thereby comparably penetrating the subject vascular vessel wall.

FIG. 28B, the distal ends of needles 66, 68 are substantially captured within needle retainer guides 342a, 342b, respectively (only the proximal ends of needles 66, 68 are depicted in FIG. 28B). The distal ends of needles 66, 68 are staggered or offset such that the distal end of needle 66 is proximally closer to the static actuation handles 360a, 360b than is the distal end of needle 68 (FIG. 28B shows the toggle bar disposed on the piercing needle ends of needles 66, 68). Suture toggle bars 340a, 340b are disposed on respective needle ends 66, 68, such that each bar protrudes from a corresponding needle end and also protrudes from a corresponding needle retainer guide 342a, 342b. The distal ends of needle retainer guides 342a, 342b are likewise staggered or longitudinally offset from each other. Each toggle bar is connected to a corresponding suture filament body 350a, 350b. In FIG. 28B, each respective filament body 350a, 350b is disposed within the lumen of a corresponding needle 66, 68, and the proximal end of each filament body protrudes outboard of the proximal end of the dynamic actuator and surface 362.

Delivery system 60 illustrated in FIG. 28B includes an outboard protrusion or cam shape 94. Cam 94 is illustrated as having two angled rib shaped or wedge shaped cam protrusions 194a, 194b disposed on the distal end of central tube 62. Respective cam protrusions 194a, 194b have corresponding distal end, cam surfaces 195a, 195b. Cam protrusions 194a, 194b splay the protruding needles during operation of the device. In FIG. 28B, respective cam protrusions 194a, 194b are staggered, or longitudinally offset, in substantially the same manner as the corresponding distal ends of needles 66, 68.

Figure 29B:
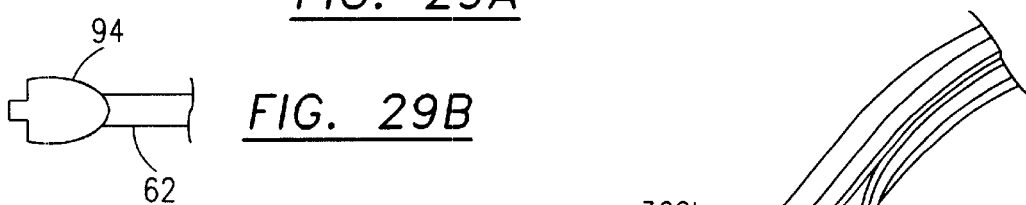
FIG. 29B diagrammatically illustrates one embodiment for the shape of the cam protruding from the delivery end of the suture delivery system.

In FIG. 28B, needle retainer guides 342a, 342b and cam protrusions 194a, 194b are attached to central tube 62. Needles 66, 68 are attached to movable member 80. Needles 66, 68 fit within needle retainer guides 342a, 342b. FIG. 29B also illustrates delivery system 60 with an actuator consisting of static user actuator bars 360a, 360b, and dynamic user actuation surface 362. Static actuator bars 360a, 360b are attached to central tube 62. Dynamic actuation surface 362 is disposed on movable member 80 and includes support 368 (illustrated as a cross-section in FIG. 28B).

Delivery system 60 in FIG. 28C is similar to system 60 in FIG. 28B. FIG. 28C diagrammatically illustrates the distal end of delivery system 60 with needles 66, 68 each having a suture toggle bar 340a, 340b disposed on the piercing needle end 67, 67a respectively. In FIG. 28C, the needles 66, 68 are shown splayed outward due to cam 94. Cam 94 has a sloped, outboard extending transitional region which is a continuously curved shape (or a substantially conical shape). The cam 94 has a proximal, cylindrical region 410 leading to the outboard sloped transitional region 412 and terminates in a distal cylindrical region 414. The distal end 94a is an angled, distally truncated end such that cam surface 94a will substantially come into contact with the vascular vessel wall 31 when the device is in use. The plane defined by cam surface 94a is parallel with the line defined by piercing needle ends 67, 67a. Each needle 66, 68 is retained by a corresponding needle guide 342a, 342b. Needles retainer guides 342a, 342b are attached to central tube 62. Central tube 62 protrudes through vessel wall 31. This figure also shows needle 68 longer than needle 66. The following exemplary dimensional table pertains to FIG. 28C.

| Typical Exemplary Dimensional Table (FIG. 28C) | | |
|---|---|---|
| a | maximum vascular wall thickness | 3 mm (approx.) |
| b | inside diameter of vascular vessel | 9 mm (approx.) |
| c | distance between shorter needle 66 and central tube 62 at point of penetration into vascular wall | 2 mm (approx.) |
| d | distance between longer needle 68 and central tube 62 at point of penetration into vascular wall | 2 mm (approx.) |
| e | distance between inner walls of needles 66, 68 at point of penetration of vascular vessel wall | 6 mm (approx.) |

Suture delivery system 60 in FIGS. 28B and 28C operates similar to delivery system 60 in FIGS. 18 and 26. The operator guides the delivery system into proper position near blood vessel 31. When positioning delivery system 60 to suture an artery, the user may orient longer needle 68 in the direction of the heart. Suture delivery system 60 may include orientation marks or indicia such as a symbol of a heart 420 (FIG. 39) and arrow 422 (FIG. 39) on the side of the system with the longer needle and a symbol of a foot 424 (FIG. 39) and arrow 426 (FIG. 39) on the side of the system with the shorter needle. Different colors could also be used on the needle retainer guides to indicate proper orientation. A pre-aligned guide wire may also be utilized to properly position the delivery system 60 at the location requiring suturing. Central tube 62 may be hollow and its lumen provides a guide for a guide wire. The operator positions suture delivery system 60 at the desired location and places the distal end of central tube 62 at or in the subject opening or aperture. See FIG. 17 and opening 44. The device is properly positioned when blood "flashes" back through or flows proximally towards the operator through the lumen of central tube 62. In FIG. 28B, central tube 62 shows a flash tube exit port 361 at a proximal location (see also FIG. 30, port 361). Alternatively, a small "flashtube" can be disposed on the central tube to indicate proper positioning of delivery system 60. Proper positioning may also be indicated when cam protrusion distal surfaces 195a, 195b in FIG. 28B or surface 94a in FIG. 28C come into contact with vascular vessel wall 31 (see also FIG. 29A, cam distal surface 94a).

The operator then utilizes static user actuator bars 360a, 360b (FIG. 28B) to stabilize the suture delivery system 60 relative to the suture delivery site. This can be accomplished by placing fingers on the distal edge of user actuator bars 360a, 360b. Alternatively, the suture delivery system 60 can be held stationary relative to the delivery site through a locking mechanism securing the system to a previously positioned guide wire (not shown). Once stabilized, the operator uses a free finger or thumb to apply force in the direction of arrow 394 to dynamic actuation surface 362. The force causes dynamic actuation surface 362 and attached movable member 80 and needles 66, 68 to move in the direction of arrow 394. As the movable member 80 moves through a maximum throw or displacement 366, the piercing needle ends of needles 66, 68 exit needle retainer guides 342a, 342b, move laterally outward as forced by cam shape 94, and extend forward (distally) into the vascular vessel wall 31, setting or embedding the suture toggle bars 340a, 340b within the vascular vessel wall 31. Each embedded suture then has a respective filament body 350a, 350b extending outboard in a proximal direction. Before extraction of the delivery system 60, a force is applied to user actuation surface 362 in the opposite direction of arrow 394 causing the piercing needle ends 66 and 68 to retract back into the needle retainer guides 342a, 342b. The force may be manually applied or may be provided by a spring (not shown).

FIG. 29A diagrammatically illustrates an enlarged cross-sectional view of the delivery end of suture delivery system 60 with its delivery needles 66 and 68 retracted. See needle 66 in guide tube 342a. One needle 66 is loaded with a suture 350a and a toggle bar 340a slightly protrudes from needle 66 and also protrudes from needle retainer guide 342a. Alignment of the needle slot and guide slot is illustrated herein. Suture filament body 350a travels proximally through the lumen of needle 66. The outboard protrusion or cam in FIG. 29A has a distally truncated, continuously curved cam body shape. The truncated surface 94a at the distal end, is normal to the longitudinal aspect of the central tube 62. As discussed earlier in connection with cam surfaces 195a, 195b in delivery system 60 illustrated in FIG. 28B, distal end surface 94a can be utilized as a stop when positioning the delivery device prior to depositing the sutures in the blood vessel. As diagrammatically illustrated in FIG. 28B, central tube 62 is inserted fully or partially into the vascular wall 31 until the vascular wall comes in contact with the distal cam surface 94a, indicating that the delivery device is in proper position. As previously discussed, a flash tube may also be utilized to show correct positioning of delivery system 60.

FIG. 29B diagrammatically illustrates cam 94 protruding from the delivery end of the suture delivery system 60. Cam 94 has a distally truncated, continuously curved shape. Cam 94 in FIG. 29B has a convex shape.

Figure 30:
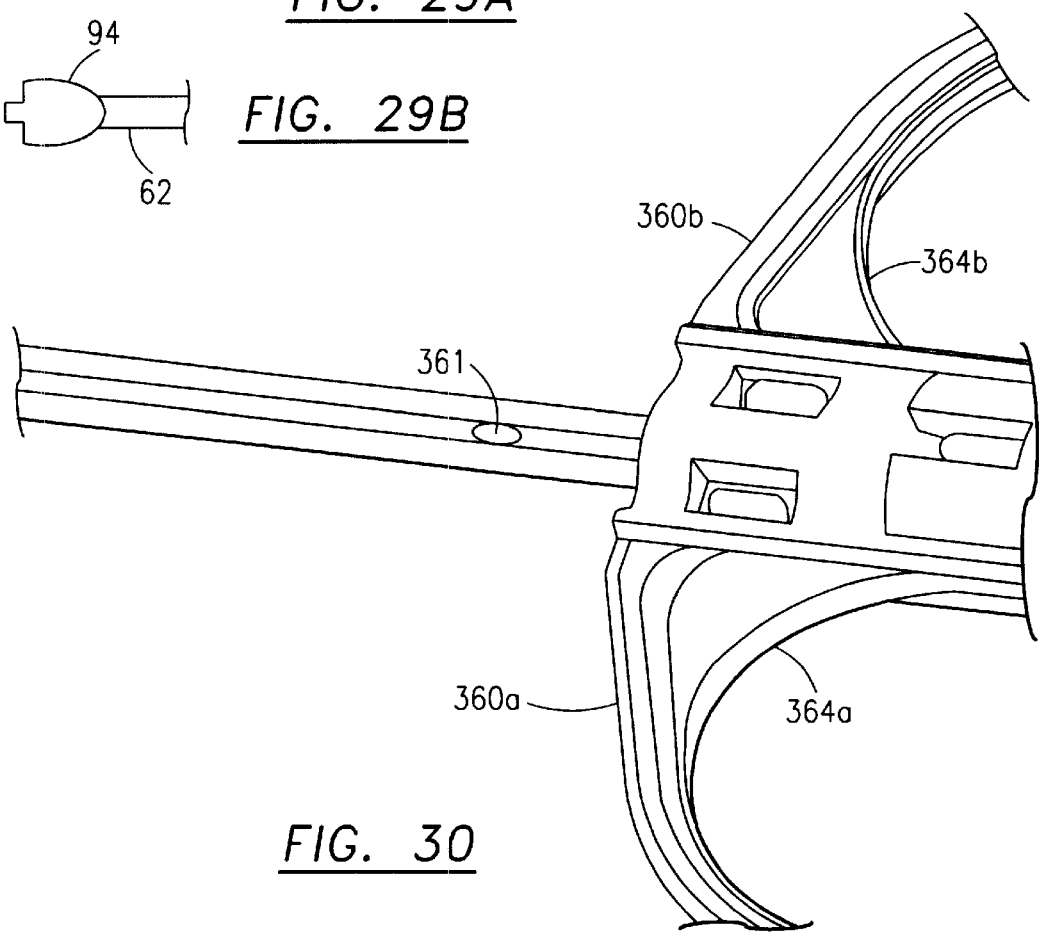
FIG. 30 diagrammatically illustrates another embodiment of the suture delivery system.

FIG. 30 diagrammatically illustrates another embodiment of the suture delivery system with actuation surfaces 360a and 360b having ribbed support structures 364a and 364b. The support structures 364a, 364b provide support for the static actuator element discussed below in connection with FIG. 31. The support structures 364a, 364b also transfer the longitudinally directed force applied during operation of the device to the axial centerline of the system. Support structures 364a, 364b also provide a planar surface in the longitudinal aspect of the instrument which enables an operator of the system greater control of the instrument when positioning the instrument.

Figure 31:
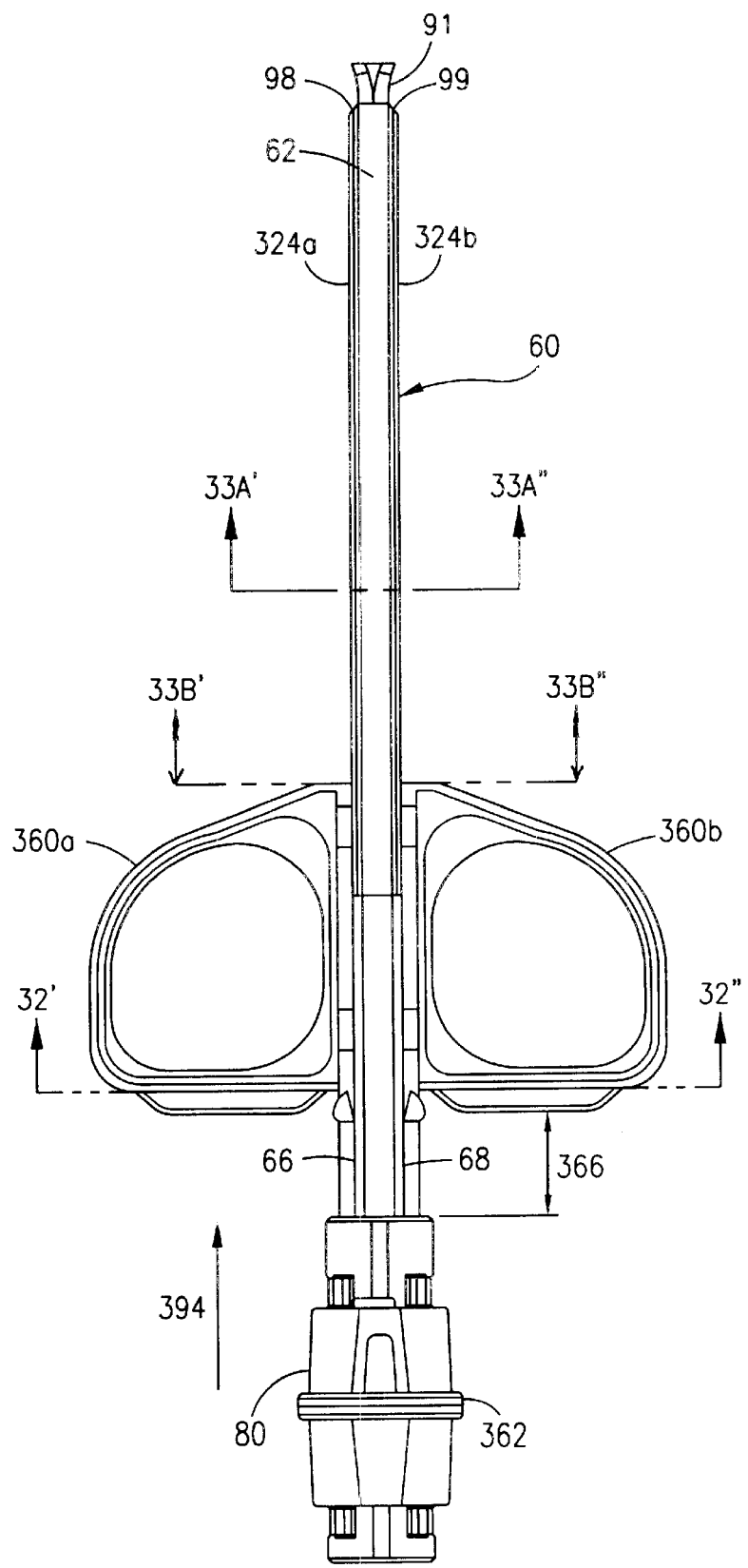
FIG. 31 diagrammatically illustrates a further embodiment of the suture delivery system.

FIG. 31 diagrammatically illustrates another embodiment of the suture delivery system 60 with an actuator consisting of a static actuator element with user actuation surfaces 360a and 360b. Surfaces 360a, 360b define a closed-loop, finger grip shape. The static actuator is attached to central tube 62. The actuator also includes a dynamic actuator element with a user actuation surface 362 consisting of finger tabs 382a, 382b (illustrated in FIG. 34). The dynamic actuator and surface 362 with finger tabs 382a, 382b are attached to movable member 80. The user actuator surfaces can be simple tabs protruding from the central tube 62 and movable member 80 rather than finger grips (see, e.g. FIG. 28B). Alternatively, as previously discussed in connection with FIG. 28B, user actuation surfaces 360a and 360b can be eliminated altogether by providing alternative means to fix the delivery system relative to the delivery site such as by providing a locking mechanism to lock the delivery system to a previously positioned guide wire.

The delivery system in FIG. 31 operates in the same manner as the delivery system diagrammatically illustrated in FIGS. 18, 26 and 28B. In the illustrated embodiment, piercing needles 66 and 68 are substantially captured within needle retainer guides 342a, 342b (only the proximal ends of needles 66, 68 are depicted in FIG. 31). The system delivers sutures through application of force in the direction 394 applied to user actuation tabs 382a, 382b (see FIG. 34) which are coupled to movable member 80. As movable member 80 slides or moves longitudinally towards the distal end of central tube 62 (a fixed or static member), the piercing needle ends of needles 66 and 68 (not shown in FIG. 31; see FIG. 29A), which are attached to movable member 80, exit needle retainer guides 342a, 342b at distal ends 98 and 99. At its maximum stroke or throw 366, the piercing needles ends have been forced laterally outward by cam shape 94, and have extended forward (distally) into the targeted bodily substructure, setting or embedding the toggle bars into the bodily substructure with the suture filaments leading outboard in a proximal direction. Before extraction of delivery system 60, a force is applied in the opposite direction of arrow 394 causing needles 66 and 68 (see FIG. 29A) to retract back into needle retainer guides 342a and 342b. Alternatively, movable member 80 with its attached needles 66, 68 is proximally biased with respect to central tube 62 such that upon removal of the force necessary to embed the sutures, movable member 80 returns to its original position with the piercing needle ends substantially within needle retainer guides 342a, 342b.

Figure 32:
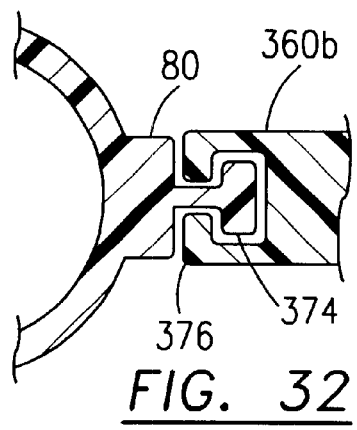
FIG. 32 is a partial, cross-sectional, detail view of the suture delivery system generally from a portion of the perspective of section line 32'-32" in FIG. 31.

FIG. 32 is a partial cross-sectional view of the suture delivery system from the perspective of section line 32'–32" in FIG. 31. FIG. 32 illustrates the coupling between movable member 80 and user actuation surface 360b (User actuation surface 360b is attached to central tube 62—see FIG. 31). In FIG. 32, movable member 80 includes a key 374 and user actuation surface 360b defines a key way 376. Key 374 and key way 376 can be reversed. The salient feature is to provide controlled longitudinal movement by movable member 80 with respect to central tube 62. Lateral movement or twisting is limited or eliminated by a key running in a key track. Movable member 80 can also consist of simple key rails adapted to slide along key way channels defined by central tube 62 or its attached static actuator. Likewise, the key and key way can be reversed.

Figure 33B:
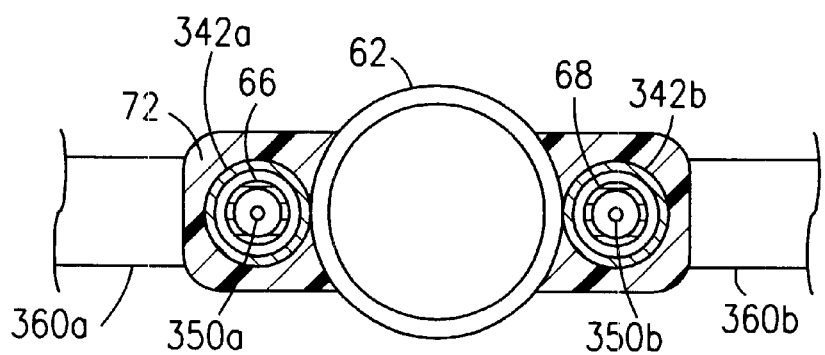
FIG. 33B is a cross-sectional view of the suture delivery system from the perspective of section line 33B'-33B" in FIG. 31.
Figure 33A:
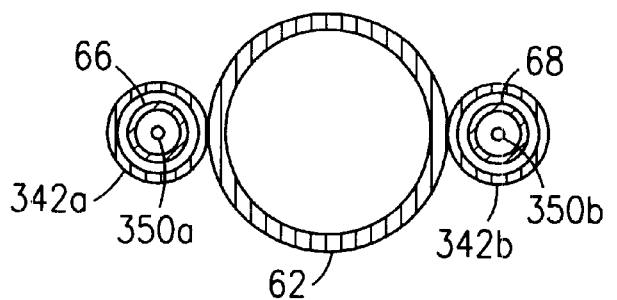
FIG. 33A is a cross-sectional view of the suture delivery system generally from a portion of the perspective of section line 33A'-33A" in FIG. 31.

FIG. 33A is a cross-sectional view of the suture delivery system from the perspective of section line 33A'–33A" in FIG. 31. FIG. 33A illustrates needle retainer guides 342a and 342b attached to central tube 62, each containing needles 66 and 68, respectively, and each needle containing suture filament bodies 350a and 350b, respectively.

FIG. 33B is a cross-sectional view of the suture delivery system from the perspective of section line 33B'–33B" in FIG. 31. In FIG. 33B, needle retainer structure 72 is connected to central tube 62, needle retainer guides 342a, 342b, and actuator static actuation surfaces 360a and 360b. FIG. 33B also shows needles retainer guides 342a and 342b containing needles 66 and 68, respectively, and each needle containing suture filament bodies 350a and 350b, respectively.

Figure 34:
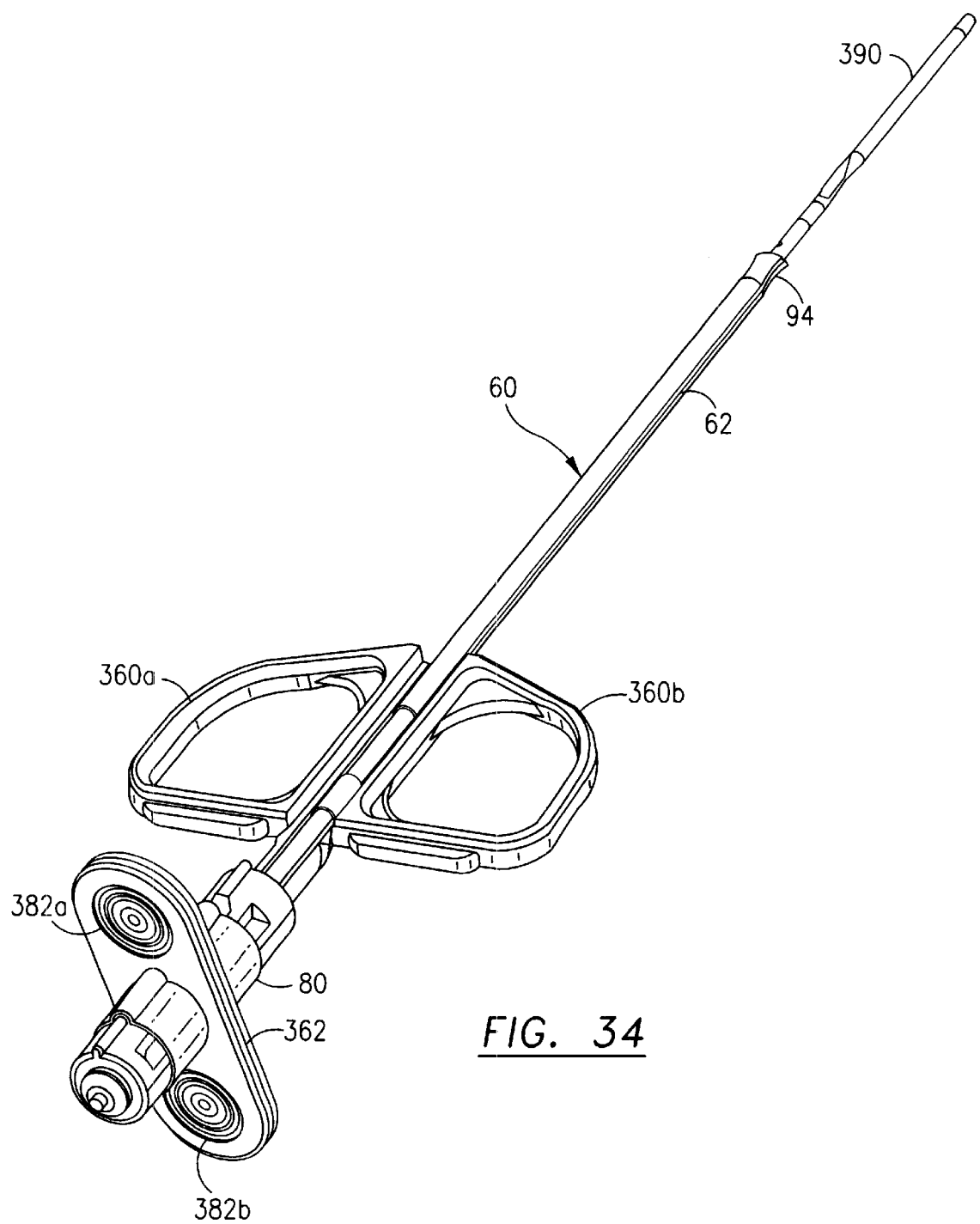
FIG. 34 diagrammatically illustrates aperspective view of the suture delivery system in FIG. 31 (and also shows a flexible tip introducer)

FIG. 34 is a diagrammatic, perspective view of suture delivery system 60 in FIG. 31. Dynamic actuation surface 362, defined by opposing finger tabs 382a, 382b extending away from central tube 62, are depicted normal to static actuation grips 360a and 360b. Delivery system 60 illustrated in FIGS. 31 and 34 can be operated by insertion of fingers within the loops of static actuation grips 360a and 360b, and the placement of the thumb or a free finger on one of the dynamic actuation finger tabs 382a, 382b. Alternatively, the user can place fingers on the distal side of static actuation grips 360a and 360b, and place the thumb or another free finger on one of the dynamic actuation finger tabs 382a, 382b. FIG. 34 also diagrammatically illustrates a flexible tip introducer 390 attached to central tube 62 at its distal end. An operator uses introducer 390 to position delivery system 60 at the subject opening or aperture (see FIG. 17, opening 44, vascular wall 31) in a vascular wall 31 by inserting the introducer through the opening 44. Cam shape 94 in FIG. 34 diagrammatically illustrates an angled rib shape.

Figure 35:
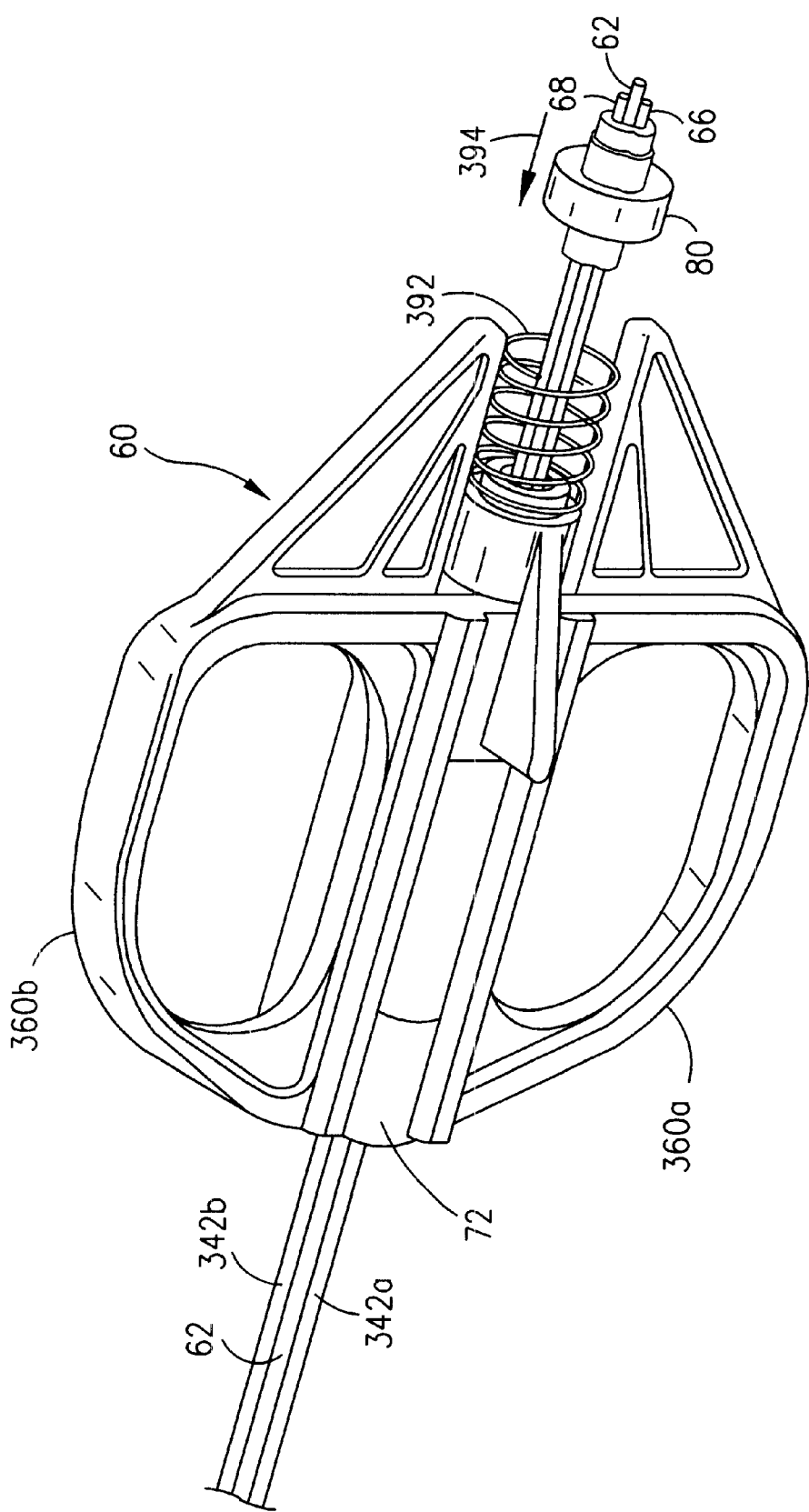

FIGS. 35 through 40 diagrammatically illustrate the proximal end of an alternative embodiment of the suture delivery system 60. FIG. 35 provides an exploded view of suture delivery system 60 (without its piercing distal end). In FIG. 35, suture delivery system 60 is depicted as having a biasing member 392 between movable member 80 and the needle retainer structure 72. Needle retainer structure 72 is attached to central tube 62 and needle retainer guides 342a, 342b. Biasing member 392 is depicted as a spring or coil in FIG. 35. The biasing member may be any type of resilient member. The suture delivery system illustrated in FIGS. 35, 36, 37, 38 and 39 operates substantially similar to the delivery system 60 illustrated in FIGS. 28B. The biasing member 392 of suture delivery system 60 in FIGS. 35 and 39 acts between movable member 80 and central tube 62 such that the piercing needle ends (not depicted in FIGS. 35 and 39) remain within the needle retainer guides 342a, 342b unless force is applied to the movable member 80 in the distal direction of arrow 394. Biasing between the movable member 80 and the central tube 62 (with attached needle retainer structure 72) can be accomplished through the use of a spring (as illustrated in FIGS. 35, 36, 37 and 39), an elastic polymer, a rubber, a sponge-like foam or another elastic material.

Figure 36:
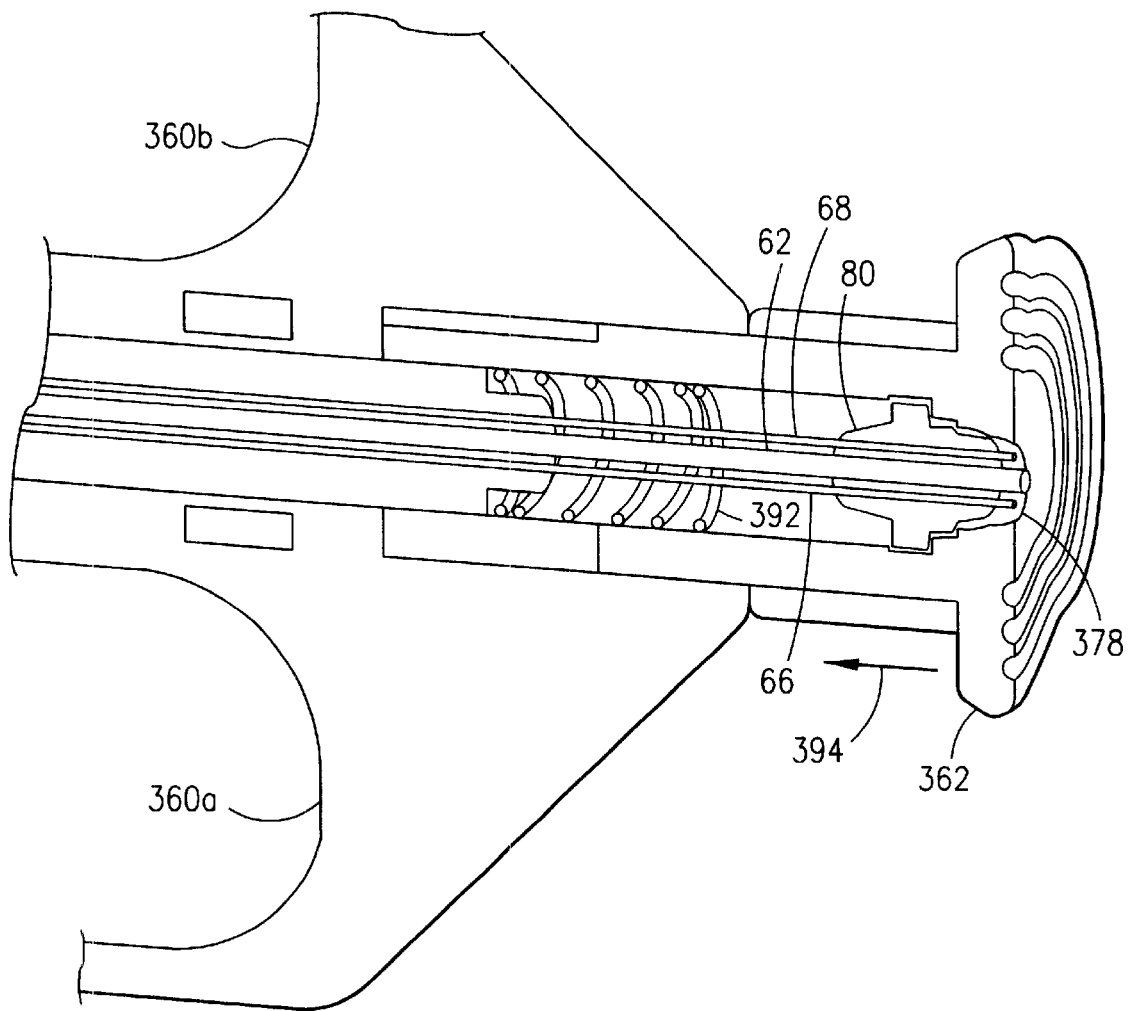

FIG. 36 is a partial cross-sectional view of FIG. 37. FIG. 36 diagrammatically illustrates the use of an actuator consisting of dynamic actuation surface tab 362 and static actuation surface grips 360a, 360b. Actuation surface tab 362 is adapted to fit over movable member 80 such that when force is applied on actuation surface tab 362 in the direction of arrow 394, surface actuation tab 362 causes movable member 80 to move in the direction of arrow 394. In FIG. 36, movable member 80 defines a cavity within which runs central tube 62. FIG. 36 also depicts needles 66 and 68 attached to movable member 80. The proximal ends of needles 66, 68 terminate at surface actuation tab 362. The proximal end of central tube 62 also terminates substantially adjacent surface actuation tab 362.

FIG. 37 illustrates the proximal end of suture delivery system 60 as illustrated in FIGS. 35 and 36. In addition to the features illustrated in FIGS. 35 and 36, FIG. 37 illustrates static actuation surface grips 360a, 360b as containing keys 372a, 372b. Dynamic actuation surface tab 362 defines corresponding key ways 370a, 370b.

FIG. 38 provides a cross-sectional view of key 372b and key way 370b from the perspective of section line 38' in FIG. 37. Alternatively, the respective keys 372a, 372b and corresponding key ways 370a, 370b between the static actuation surface grips 360a, 360b and dynamic actuation surface tab 362 may be reversed providing an equally operable suture delivery system. 1741 FIGS. 36 and 37 diagrammatically illustrate a dynamic actuation surface tab 362 with channels or ports 378 through which the proximal ends of the suture filament bodies 350a, 350b (shown only in FIG. 37) can extend proximally beyond the dynamic actuation surface tab 362. FIGS. 36 and 37 also diagrammatically illustrate channel or port 378 with the proximal end of central tube 62 extending through the dynamic actuation surface tab 62. A guide wire or other device may be inserted into the central tube 62 through the proximal end of the dynamic actuator surface 362. Alternatively, dynamic actuation surface 362 can consist of a solid proximal actuation surface with exit ports or channels on the sides of the dynamic actuation member 362. Likewise, a similar port or channel can be provided on the side of central tube 62 through which a guide wire may be inserted. Such a similar port or channel could also be used as a flashback tube or flashback indicator.

Figure 39:
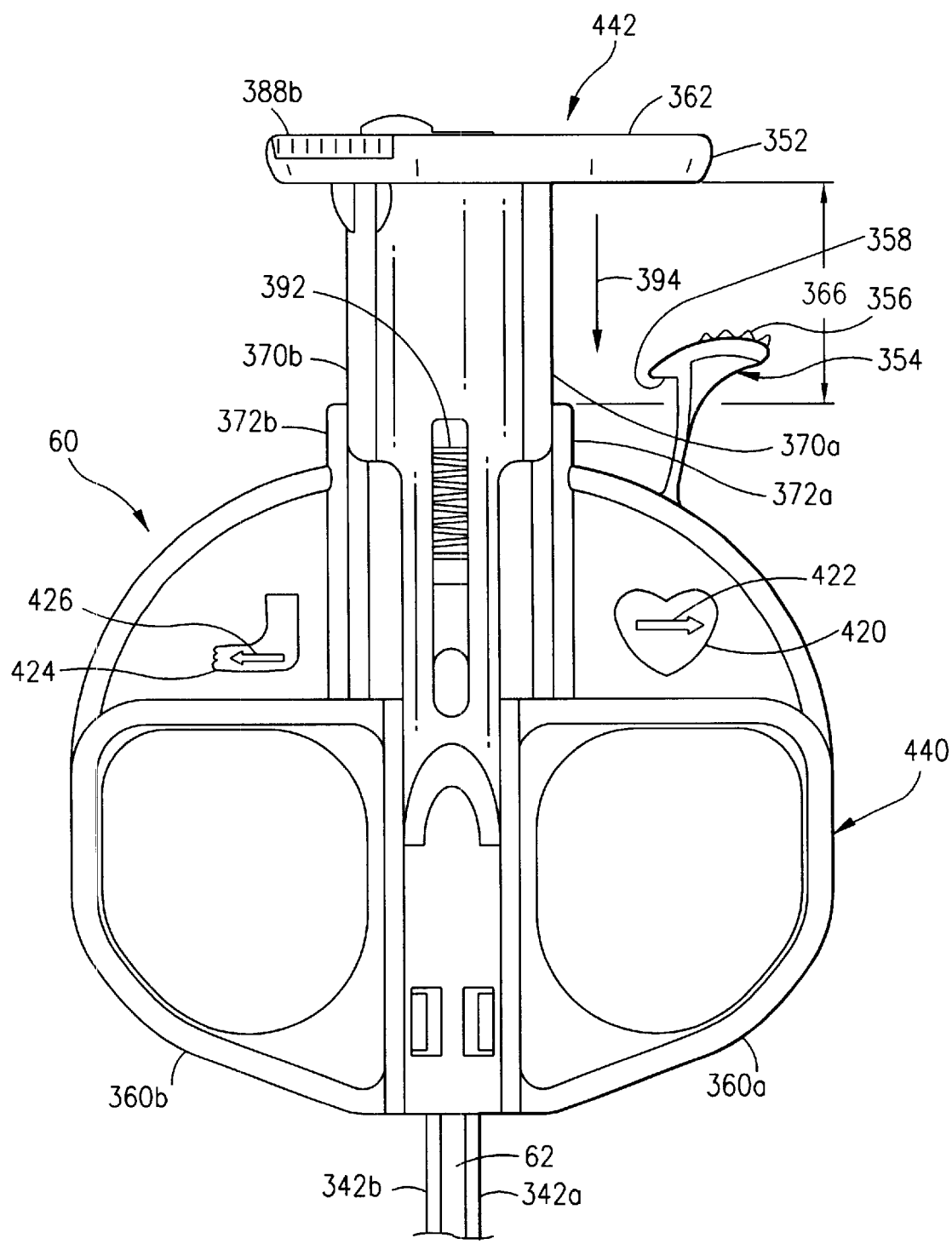
Figure 40:
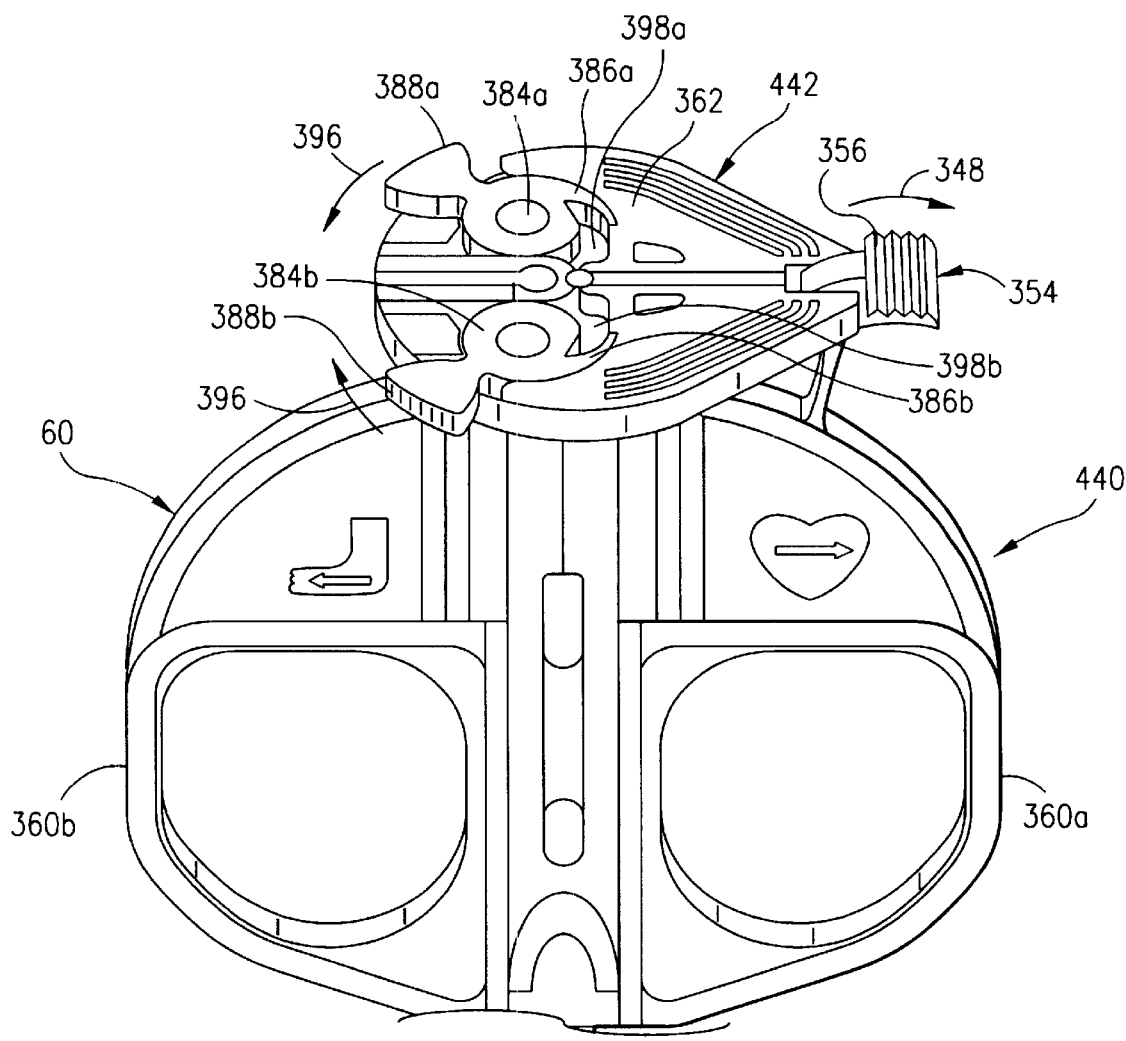
FIG. 40 is a partial perspective view of the alternative embodiment shown in FIG. 39.

FIG. 39 is a partial side view of the proximal end of an alternative embodiment of suture delivery system 60. FIG. 40 is a partial perspective view of the delivery system 60 illustrated in FIG. 39. Suture delivery system 60 in FIGS. 39 and 40 are substantially similar, and therefore, the components of system 60 depicted in FIGS. 39 and 40 are discussed concurrently. Suture delivery system 60 in FIGS. 39 and 40 is substantially similar to system 60 in FIGS. 35–38 with additional components. Most notably is locking member 354, shown disposed onto user actuator 440 defining actuation surface 360a (which also defines part of key 372a). Locking member 354 may also be disposed on to user actuation surface 360b. Locking member 354 can be attached to actuator 440 by means of a hinge, screw, glue or other traditional means. In the preferred embodiment shown in FIGS. 39 and 40, locking member 354 is cast in plastic as part of user actuator 440 and includes leg 430 attaching locking member 354 to actuator 440. Locking member 354 also includes locking catch 358 and locking member grip surface 356. Locking catch 358 interacts with the top, corner edge 352 of user actuator 442 which defines dynamic actuation surface 362. In an alternative embodiment, locking member 354 is disposed on user actuator 442 and the locking catch is adapted to interact with a corresponding catch element on central tube 62 or attached user actuator 440.

Suture delivery system 60 in FIG. 40 shows cutting members 384a, 384b. Cutting members 384a, 384b include corresponding cutting blades (not shown) attached to cutting members 384a, 384b. Cutting members 384a, 384b also include corresponding limiting elements 386a, 386b. Limiting elements 386a, 386b are shown in FIG. 40 as part of cutting members 384a, 384b, respectively. However, limiting elements 386a, 386b can be separate elements attached to cutting members 384a, 384b. Cutting members 384a, 384b are disposed onto user actuator 442. Cutting members 384a, 384b can be attached to user actuator 442 by means of a pin, rivet, nut and bolt, or any suitable means permitting the rotating cutting members 384a, 384b to rotate. Cutting members 384a, 384b also include corresponding user actuation surfaces 388a, 388b, depicted as knurled surfaces on ear-shaped projections in FIG. 40.

Operation of suture delivery system 60 in FIGS. 39 and 40 is similar to system 60 in FIG. 28B and 28C, but includes additional enhancements. Locking member 354 provides a means to lock delivery system 60 in a position with needles 66, 68 (see FIG. 28C) in a fully extended position. During operation of suture delivery system 60 the user depresses dynamic actuation surface 362 of actuator 442 in the direction of arrow 394 while holding system 60 static or steady through use of user actuation surfaces 360a, 360b. Once the user depresses dynamic actuator 442 such that suture delivery system 60 undergoes a full stroke or throw (shown by displacement arrows 366), the user pulls locking member 354 radially outboard in the direction 348 (FIG. 40), to allow catch 358 to engage corner 352. The user then pushes member 354 radially inboard onto corner 352 to lock the system in a fully engaged position. Once the user is ready to extract or remove suture delivery system 60 from the delivery site (after deposition of the suture toggles), the user once again pulls member 354 radially outboard in direction 348, thereby releasing dynamic actuation surface 362. The user can then pull user actuator 442 in a proximal direction opposite arrow 394 or allow biasing member 392 to return system 60 to its original proximal position. Alternatively, prior to disengaging locking member 354, the user may want to cut the suture threads extending outboard of the suture delivery site (see suture threads 350a, 350b in FIG. 37). The user may accomplish cutting of the suture threads by rotating cutting members 384a, 384b in the direction of arrows 396 towards the centerline of dynamic actuator 442. Prior to rotating cutting members 384a, 384b, limiting elements 386a, 386b are in cavities 398a, 398b, respectively. When the user rotates cutting members 384a, 384b in direction 396 through the use of user surfaces 388a, 388b, respectively, the corresponding limiting elements 386a, 386b snap into corresponding notches on dynamic actuation surface 362 (see FIG. 40). As the rotating cutting members 384a, 384b rotate, the corresponding attached blades cut the suture threads running outboard of the suture delivery system 60 through dynamic actuation surface 362 (see FIG. 37).

The following is a table of exemplary dimensions of the suture delivery system claimed in this invention:

| Typical Exemplary Dimension Table | |
|---|---|
| Cam or needle guide length | 4 mm (approx.) |
| Cam or needle guide lateral span | 4 mm (approx.) |
| Apparatus total length | 15–18 cm (approx.) |
| Stroke or throw | 5–18 mm (approx.) |
| Finger grip or static actuator | 6 cm (approx.) |
| Needle bevel | 1 mm (approx.) |
| Needle slot | 1 mm (approx.) |

The claims appended hereto are meant to cover modifications and changes within the scope and spirit of the present invention.

What is claim is:

1. A suture delivery system comprising:
   two sutures, each said suture having a filament body and toggle bar on at least one terminal end thereof;
   an elongated central tube, said central tube carrying two needle retainer guides and a cam distally disposed on said central tube;
   two spaced apart needles with piercing needle ends, each corresponding needle end carrying a respective suture with a respective toggle bar disposed on said corresponding needle end such that a portion of said toggle bar protrudes from said corresponding needle end;
   a movable member longitudinally movably mounted on said central tube, each said needle coupled to said movable member;
   each respective needle movably disposed and guided by a corresponding needle retainer guide;
   an actuator coupled to said movable member, said actuator adapted to longitudinally move said movable member with respect to said central tube such that said needles are substantially captured by said needle retainer guides when said movable member is at a proximal position, and said piercing needle ends move over said cam when said movable member is at a distal position.

2. A suture delivery system as claimed in claim 1 wherein each piercing needle end is substantially captured within a corresponding needle retainer guide when said movable member is in said proximal position, and wherein each piercing needle end splays outward due to said cam when said movable member is in said distal position.

3. A suture delivery system as claimed in claim 1 wherein said actuator includes a first user actuation surface, said first user actuation surface being coupled to said movable member, and wherein said central tube includes a second user actuation surface, said second user actuation surface being coupled to said central tube, said movable member adapted to move longitudinally with respect to said central tube via said first and second user actuation surfaces.

4. A suture delivery system as claimed in claim 1 wherein said central tube includes a static actuation surface, said static actuation surface being coupled to said central tube, and said actuation surface including a finger tab.

5. A suture delivery system as claimed in claim 1 wherein said actuator includes a dynamic actuation surface, said dynamic actuation surface being coupled to said movable member, and said dynamic actuation surface including a finger actuation surface.

6. A suture delivery system as claimed in claim 1 wherein said actuator includes a first and a second actuation surface, said first actuation surface being coupled to said movable member, said first actuation surface including a finger actuation surface, and said second actuation surface being coupled to said central tube, said second actuation surface including a finger tab.

7. A suture delivery system as claimed in claim 1 wherein said central tube includes a distal central tube end, said cam being mounted at said distal tube end or spaced apart from said distal tube end;
   said needle retainer guides proximally mounted near said cam;
   said actuator including a first actuation surface, said first actuation surface proximally mounted on said movable member;
   said central tube including a second actuation surface, said second actuation surface mounted on said central tube such that said first and second actuation surfaces are adapted to be moved relative to each other; and
   said distal tube end and said piercing needle ends are disposed substantially adjacent each other when said movable member is at said distal position, and said needle ends are substantially captured by said needle retainer guides when said movable member is at said proximal position.

8. A suture delivery system as claimed in claim 1 wherein each said respective needle has a hollow lumen, each said respective needle having disposed therein a corresponding filament body when said corresponding toggle bar is disposed at said respective needle end.

9. A suture delivery system as claimed in claim 8 wherein said actuator includes an actuation surface, said actuation surface being coupled to said movable member, and each respective needle having a proximal needle end through which runs a corresponding filament such that said corresponding filament body extends beyond said actuation surface.

10. A suture delivery system as claimed in claim 8 wherein said actuator includes an actuation surface defining exit ports, said actuation surface being coupled to said movable member, and each respective needle having a proximal needle end through which runs a corresponding filament body, and said corresponding filament body extends outboard through a respective actuation surface exit port.

11. A suture delivery system as claimed in claim 1 wherein each said needle end includes a respective slot adapted to capture said toggle bar thereat, each said respective toggle bar is either at an acute angle with respect to the corresponding filament body such that said acute angle is in said respective slot, or said toggle bar is normal with respect to said corresponding filament body and said respective toggle bar protrudes beyond the corresponding needle slot.

12. A suture delivery system as claimed in claim 1 wherein each said suture is made of one of a wire and a suture thread.

13. A suture delivery system as claimed in claim 1 wherein each said needle end includes a respective slot adapted to capture said toggle bar thereat, and wherein said each said toggle bar includes a catch element, said catch element is one of a leg, a tab, a protrusion, and an extension from said toggle bar, said catch element coacts with said respective slot on a corresponding needle.

14. A suture delivery system as claimed in claim 1 wherein said cam is an outboard protrusion having one shape from the group including a spherical shape, an olive shape, an oblong shape, a frustoconical shape, a convex frustoconical shape, a concave frustoconical shape, a triangular shape, a conical shape, an angled rib shape and a distally truncated, continuously curved shape.

15. A suture delivery system as claimed in claim 1 wherein said movable member is biased with respect to said central tube to place said movable member in said proximal position thereby causing said needle ends to be substantially captured by said needle retainer guides.

16. A suture delivery system as claimed in claim 1 including a biasing element intermediate said movable member and said central tube, placing said movable member in said proximal position thereby causing said needle ends to be substantially captured by said needle retainer guides.

17. A suture delivery system as claimed in claim 1 wherein said central tube has a lumen, said system includes a guide wire adapted to pass through said central tube lumen.

18. A suture delivery system as claimed in claim 1 wherein said two spaced apart needles are a first and second needle having first and second piercing needle ends, said first needle end is longitudinally offset from said second needle end; and
wherein said first and second needle ends are substantially captured by corresponding needle retainer guides at said proximal position.

19. A suture delivery system as claimed in claim 1 further comprising a locking member interposed between said central tube and said movable member, said locking member adapted to lock said position of said movable member relative to said central tube.

20. A suture delivery system as claimed in claim 1 further comprising an elongated flexible introducer disposed at a distal end of said central tube.

21. A suture delivery system as claimed in claim 3 wherein said first user actuation surface includes a finger actuation surface.

22. A suture deliver system as claimed in claim 21 wherein said second user actuation surface includes a finger tab.

23. A suture delivery system as claimed in claim 22 wherein said movable member is biased with respect to said central tube to place said movable member in said proximal position thereby causing said needle ends to be substantially captured by said needle retainer guides.

24. A suture delivery system as claimed in claim 23 further comprising a locking member interposed between said central tube and said movable member, said locking member adapted to lock said position of said movable member relative to said central tube.

25. A suture delivery system adapted to deliver two sutures, each said suture having a filament body with a toggle bar on at least one terminal end thereof, comprising:
an elongated central tube, said central tube carrying two needle retainer guides and a cam distally disposed on said central tube;
two spaced apart needles with piercing needle ends, each corresponding needle end adapted to carry a respective suture with a respective toggle bar disposed on said corresponding needle end such that a portion of said toggle bar protrudes from said corresponding needle end;
a movable member longitudinally movably mounted on said central tube, each said needle coupled to said movable member;
each respective needle movably disposed and guided by a corresponding needle retainer guide;
an actuator coupled to said movable member, said actuator adapted to longitudinally move said movable member with respect to said central tube such that said needles are substantially captured by said needle retainer guides when said movable member is at a proximal position, and said piercing needle ends move over said cam when said movable member is at a distal position.

26. A suture delivery system as claimed in claim 25 wherein said actuator includes a first user actuation surface, said first user actuation surface being coupled to said movable member, and wherein said central tube includes a second user actuation surface, said second user actuation surface being coupled to said central tube, said movable member adapted to move longitudinally with respect to said central tube via said first and second user actuation surfaces.

27. A suture delivery system as claimed in claim 25 wherein said central tube includes a static actuation surface, said static actuation surface being coupled to said central tube, and said actuation surface including a finger tab.

28. A suture delivery system as claimed in claim 25 wherein said actuator includes a dynamic actuation surface, said dynamic actuation surface being coupled to said movable member, and said dynamic actuation surface including a finger actuation surface.

29. A suture delivery system as claimed in claim 25 wherein said movable member is biased with respect to said central tube to place said movable member in said proximal position thereby causing said needle ends to be substantially captured by said needle retainer guides.

30. A suture delivery system as claimed in claim 25 wherein said two spaced apart needles are a first and second needle having first and second piercing needle ends, said first needle end is longitudinally offset from said second needle end; and
wherein said first and second needle ends are substantially captured by corresponding needle retainer guides at said proximal position.

31. A suture delivery system as claimed in claim 25 further comprising an elongated flexible introducer disposed at a distal end of said central tube.

32. A suture delivery system as claimed in claim 25 further comprising a locking member interposed between said central tube and said movable member, said locking member adapted to lock said position of said movable member relative to said central tube.

33. A suture delivery system as claimed in claim 26 wherein said first user actuation surface includes a finger actuation surface, said second user actuation surface includes a finger tab, and said movable member is biased with respect to said central tube to place said movable member in said proximal position thereby causing said needle ends to be substantially captured by said needle retainer guides.

34. A suture delivery system comprising:
at least one suture, said at least one suture having a filament body with at least one terminal end and a toggle bar thereat;
an elongated central tube, said central tube carrying at least one needle retainer guide and a cam distally disposed on said central tube;
at least one needle with a piercing needle end, said needle end carrying said filament body with said toggle bar disposed on said needle end such that a portion of said toggle bar protrudes from said needle end;
a movable member longitudinally movably mounted on said central tube with said at least one needle coupled to said movable member;
said at least one needle movably disposed and guided by said at least one needle retainer guide;
an actuator coupled to said movable member, said actuator adapted to longitudinally move said movable member with respect to said central tube such that said at least one needle is substantially captured by said at least one needle retainer guide when said movable member is at a proximal position, and said piercing needle end moves over said cam when said movable member is at a distal position.

35. A suture delivery system as claimed in claim 34 wherein said actuator includes a first user actuation surface, said first user actuation surface being coupled to said movable member, and wherein said central tube includes a second user actuation surface, said second user actuation surface being coupled to said central tube, said movable member adapted to move longitudinally with respect to said central tube via said first and second user actuation surfaces.

36. A suture delivery system as claimed in claim 34 wherein said central tube includes a static actuation surface, said static actuation surface being coupled to said central tube, and said actuation surface including a finger tab.

37. A suture delivery system as claimed in claim 34 wherein said actuator includes a dynamic actuation surface, said dynamic actuation surface being coupled to said movable member, and said dynamic actuation surface including a finger actuation surface.

38. A suture delivery system as claimed in claim 34 wherein said movable member is biased with respect to said central tube to place said movable member in said proximal position thereby causing said at least one needle with a piercing needle end to be substantially captured by said at least one needle retainer guide.

39. A suture delivery system as claimed in claim 34 wherein said first user actuation surface includes a finger actuation surface, said second user actuation surface includes a finger tab, and said movable member is biased with respect to said central tube to place said movable member in said proximal position thereby causing said piercing needle end of said at least one needle to be substantially captured by said at least one needle retainer guide.

40. A suture delivery system as claimed in claim 34 further comprising an elongated flexible introducer disposed at a distal end of said central tube.

41. A suture delivery system as claimed in claim 34 further comprising a locking member interposed between said central tube and said movable member, said locking member adapted to lock said position of said movable member relative to said central tube.

42. A suture delivery system as claimed in claim 34 wherein said filament body of said at least one suture includes two terminal ends each having a respective toggle bar thereat, the delivery system including two needles each with a respective piercing needle end and including two needle retainer guides, said needle retainer guides carried by said central tube, each said respective toggle bar disposed on a corresponding needle end wherein each said respective piercing needle end moves over said cam when said movable member is at said distal position.

43. A suture delivery system as claimed in claim 42 wherein said two needles are a first and second needle having first and second piercing needle ends, said first needle end is longitudinally offset from said second needle end; and
wherein said first and second needle ends are substantially captured by corresponding needle retainer guides at said proximal position.

44. A method for embedding sutures in a vascular wall or other biological substructure, each said suture having a filament body with a toggle bar on its terminal end, comprising the steps of:
providing at least two needles having piercing needle ends;
retaining a respective toggle bar on a corresponding piercing needle end;
splaying said needles outward and forward towards and into said vascular wall or other biological substructure;
setting, with said needles, said respective toggle bar in said vascular wall or other biological substructure with its corresponding filament body leading outboard to a proximal position; and
substantially covering said needle ends after said setting step.

45. A method as claimed in claim 44 wherein said needle ends are substantially covered before said splaying step and after said setting step.

46. A method as claimed in claim 44 wherein said method for embedding said sutures in said vascular wall includes the step of providing a blood flow path through said vascular wall to a proximal position, said blood flow path being indicative of a step of placement of said needles adjacent said vascular wall, said placement step occurring prior to said splaying step.

47. A method as claimed in claim 44 wherein said sutures are embedded in said vascular wall, said method includes the step of penetrating said vascular wall and positioning said needle ends at said vascular wall prior to said splaying step.

48. A method as claimed in claim 44 including the step of capturing said filament body during the steps of retaining, splaying and setting.

49. A method as claimed in claim 44 including controlling of said splaying outward and forward movement of said needles and providing an operator control therefor.

50. A method as claimed in claim 49 wherein said controlling step is a manual step.

51. A method as claimed in claim 44 wherein said step of retaining said respective toggle bar on said corresponding needle end includes the step of enabling protrusion of said toggle bar beyond said corresponding needle end.

52. A method as claimed in claim 44 including the step of biasing said needles to substantially cover said needle ends other than during said splaying and setting steps.

53. A method as claimed in claim 44 wherein said step of splaying includes the step of splaying said needle ends in a longitudinally offsetting manner.

54. A method as claimed in claim 44 including the step of cutting said filament body after said setting step.

55. A method as claimed in claim 45 wherein said method for embedding sets sutures in said vascular wall and method includes providing a blood flow path through said vascular wall to a proximal position, said blood flow path being indicative of a step of placement of said needles adjacent said vascular wall, said placement step occurring prior to said splaying step.

56. A method as claimed in claim 55 including controlling of said splaying outward and forward movement of said needles and providing an operator control therefor.

57. A method as claimed in claim 56 wherein said controlling step is a manual step.

58. A method as claimed in claim 57 including the step of biasing said needles to substantially cover said needle ends other than during said splaying and setting steps.

59. A method as claimed in claim 58 wherein said step of splaying includes the step of splaying said needle ends in a longitudinally offsetting manner.

60. A method as claimed in claim 59 including the step of cutting said filament body after said setting step.

61. A method for embedding sutures in a vascular wall or other biological substructure, each said suture having a filament body with a toggle bar on its terminal end, comprising the steps of:

providing at least two needles having piercing needle ends;

retaining a respective toggle bar on a corresponding piercing needle end with a portion of each respective toggle bar protruding from its corresponding piercing needle end;

extending said needles outward and forward towards and into said vascular wall or other biological substructure;

setting, with said needles, said respective toggle bar in said vascular wall or other biological substructure with its corresponding filament body leading outboard to a proximal position; and substantially covering said needle ends after said setting step.

62. A method as claimed in claim 61 wherein said needle ends are substantially covered before said extending step and after said setting step.

63. A method as claimed in claim 61 including the step of capturing said filament body during the steps of retaining, extending and setting.

64. A method as claimed in claim 61 including controlling of said extending outward and forward movement of said needles and providing an operator control therefor.

65. A method as claimed in claim 64 wherein said controlling step is a manual step.

66. A method as claimed in claim 61 including the step of biasing said needles to substantially cover said needle ends other than during said extending and setting steps.

67. A method as claimed in claim 61 wherein said step of extending includes the step of extending said needle ends in a longitudinally offsetting manner.

68. A method as claimed in claim 61 wherein said sutures are embedded in said vascular wall, said method includes the step of penetrating said vascular wall and positioning said needle ends at said vascular wall prior to said splaying step.

69. A method as claimed in claim 61 including the step of cutting said filament body after said setting step.

* * * * *